(12) United States Patent
Tobinick

(10) Patent No.: US 8,900,583 B2
(45) Date of Patent: Dec. 2, 2014

(54) METHODS FOR TREATMENT OF BRAIN INJURY UTILIZING BIOLOGICS

(75) Inventor: Edward Lewis Tobinick, Boca Raton, FL (US)

(73) Assignee: TACT IP LLC, Boca Raton, FL (US)

( * ) Notice: Subject to any disclaimer, the term of this patent is extended or adjusted under 35 U.S.C. 154(b) by 0 days.

(21) Appl. No.: 13/848,044

(22) PCT Filed: Oct. 31, 2011

(86) PCT No.: PCT/US2011/058573
§ 371 (c)(1),
(2), (4) Date: Mar. 20, 2013

(87) PCT Pub. No.: WO2012/061289
PCT Pub. Date: May 10, 2012

(65) Prior Publication Data
US 2013/0224197 A1    Aug. 29, 2013

Related U.S. Application Data

(60) Provisional application No. 61/409,012, filed on Nov. 1, 2010, provisional application No. 61/413,440, filed on Nov. 13, 2010, provisional application No. 61/413,444, filed on Nov. 14, 2010.

(51) Int. Cl.
| | |
|---|---|
| A61K 38/00 | (2006.01) |
| A61K 39/00 | (2006.01) |
| A61K 39/395 | (2006.01) |
| C07K 14/715 | (2006.01) |
| C07K 16/24 | (2006.01) |
| A61K 9/00 | (2006.01) |

(52) U.S. Cl.
CPC ......... *A61K 39/3955* (2013.01); *C07K 14/7151* (2013.01); *C07K 16/241* (2013.01); *A61K 9/0085* (2013.01); *A61K 2039/505* (2013.01); *C07K 2319/30* (2013.01)
USPC .................................... 424/134.1; 424/184.1

(58) Field of Classification Search
None
See application file for complete search history.

(56) References Cited

U.S. PATENT DOCUMENTS

| | | | |
|---|---|---|---|
| 6,177,077 B1 | 1/2001 | Tobinick | |
| 6,419,944 B2 * | 7/2002 | Tobinick | 424/422 |
| 2005/0152905 A1 * | 7/2005 | Omoigui | 424/145.1 |
| 2006/0009450 A1 | 1/2006 | Tobinick | |
| 2008/0019964 A1 | 1/2008 | Olmarker et al. | |
| 2009/0130019 A1 * | 5/2009 | Tobinick | 424/1.49 |
| 2013/0344081 A1 * | 12/2013 | Kaji, Ryuji | 424/145.1 |

OTHER PUBLICATIONS

Ribbers (Internat Encyc Rehabilit pp. 1-9, 2010.*
Jan. 1, 2007, Burkovetskaya, M.E., S.G. Levin, and O.V. Godukhin, *Neuroprotective effects of interleukin-10 and tumor necrosis factor-alpha against hypoxia-induced hyperexcitability in hippocampal slice neurons*. Neurosci Lett, 2007. 416(3): p. 236-40.
Jan. 1, 1995, Byrod, G., et al., *A rapid transport route between the epidural space and the intraneural capillaries of the nerve roots*. Spine, 1995. 20(2): p. 138-43.
Jan. 1, 2000, Byrod, G., et al., *Transport of epidurally applied horse-radish peroxidase to the endoneurial space of dorsal root ganglia: a light and electron microscopic study*. J Peripher Nerv Syst, 2000. 5(4): p. 218-26.
Jan. 1, 1994, Cacabelos, R., et al., *Serum tumor necrosis factor (TNF) in Alzheimer's disease and multi-infarct dementia*. Methods Find Exp Clin Pharmacol, 1994. 16(1): p. 29-35.
Jan. 1, 1998, Carlson, N.G., et al., *Nicotine blocks TNF-alpha-mediated neuro protection to NMDA by an alpha-bungarotoxin-sensitive pathway*. J Neurobiol, 1998. 35(1): p. 29-36.
Jan. 1, 1999, Carlson, N.G., et al., *Inflammatory cytokines IL-1 alpha, IL-1 beta, IL-6, and TNF-alpha impart neuro protection to an excitotoxin through distinct pathways*. J Immunol, 1999. 163(7): p. 3963-8.
Jan. 1, 2003, Chauhan, N.B. and G.J. Siegel, *Intracerebroventricular passive immunization with anti-Abeta antibody in Tg2576*. J Neurosci Res, 2003. 74(1): p. 142-7.
Jan. 1, 2010, Chio, C.C., et al., *Therapeutic evaluation of etanercept in a model of traumatic brain injury*. J Neurochem, 2010. 115(4): p. 921-9.
Jan. 1, 2010, Clark, I.A., L.M. Alleva, and B. Vissel, *The roles of TNF in brain dysfunction and disease*. Pharmacol Ther, 2010, 128: 519-548.
Aug. 1, 1999, *TNF neutralization in MS: results of a randomized, placebo-controlled multicenter study. The Lenercept Multiple Sclerosis Study Group and The University of British Columbia MS/MRI Analysis Group*. Neurology, 1999. 53(3): p. 457-65.
Jan. 1, 1994, Aisen, P.S. and K.L. Davis, *Inflammatory mechanisms in Alzheimer's disease: implications for therapy*. Am J Psychiatry, 1994. 151(8): p. 1105-13.
May 1, 1997, Aisen, P.S. and K.L. Davis, *The search for disease-modifying treatment for Alzheimer's disease*. Neurology, 1997. 48(5 Suppl 6): p. S35-41.
Feb. 1, 2000, Aisen, P.S., et al., *A randomized controlled trial of prednisone in Alzheimer's disease. Alzheimer's Disease Cooperative Study*. Neurology, 2000. 54(3): p. 588-93.
Jan. 1, 2006, Al Saieg, N. and M.J. Luzar, *Etanercept induced multiple sclerosis and transverse myelitis*. J Rheumatol, 2006. 33(6): p. 1202-4.
Feb. 5, 1996, Alvarez, X.A., et al., *Blood levels of histamine, IL-1 beta, and TNF-alpha in patients with mild to moderate Alzheimer disease*. Mol Chem Neuropathol, 1996. 29(2-3): p. 237-52.
Jan. 1, 1951, Anderson, R., *Diodrast studies of the vertebral and cranial venous systems to show their probable role in cerebral metastases*. J Neurosurg, 1951. 8(4): p. 411-22.

(Continued)

*Primary Examiner* — Daniel E Kolker
*Assistant Examiner* — Aditi Dutt
(74) *Attorney, Agent, or Firm* — Neifeld IP Law

(57) ABSTRACT

A method of using biologics to treat chronic brain injury or spasticity due to stroke, trauma and other causes. Preferred embodiments include perispinal, parenteral, transepidermal or intranasal use of TNF antagonists. The TNF antagonists include TNF receptor fusion proteins, TNF monoclonal antibodies (mAbs), humanized TNF mAbs, fully human TNF mAbs, chimeric TNF mAbs, domain TNF antibodies, mAB fragments, anti-TNF nanobodies, dominant negative TNF constructs and TNF inhibitory single chain antibody fragments. One of the preferred embodiments of this invention is the perispinal administration of etanercept for treatment of mammals following stroke. The use of Trendelenburg positioning, catheters, pumps, or depot formulations are included.

15 Claims, 6 Drawing Sheets

(56) References Cited

OTHER PUBLICATIONS

Jun. 1, 2000, Anthony, J.C., et al., *Reduced prevalence of AD in users of NSAIDs and H2 receptor antagonists: the Cache County study.* Neurology, 2000. 54(11): p. 2066-71.

Nov. 17, 2004, Apkarian, A.V., et al., *Chronic back pain is associated with decreased prefrontal and thalamic gray matter density.* J Neurosci, 2004. 24(46): p. 10410-5.

Jan. 1, 1995, Arvin, B., et al., *Brain injury and inflammation. A putative role of TNF alpha.* Ann N Y Acad Sci, 1995. 765: p. 62-71; discussion 98-9.

Jan. 1, 1996, Arvin, B., et al., *The role of inflammation and cytokines in brain injury.* Neurosci Biobehav Rev, 1996. 20(3): p. 445-52.

Jan. 1, 1995, Banks, W.A., S.R. Plotkin, and A.J. Kastin, *Permeability of the blood-brain barrier to soluble cytokine receptors.* Neuroimmunomodulation, 1995. 2(3): p. 161-5.

Sep. 1, 1995, Barger, S.W., et al., *Tumor necrosis factors alpha and beta protect neurons against amyloid beta-peptide toxicity: evidence for involvement of a kappa B-binding factor and attenuation of peroxide and Ca2+ accumulation.* Proc Natl Acad Sci U S A, 1995. 92(20): p. 9328-32.

Jan. 1, 1997, Barone, F.C., et al., *Tumor necrosis factor-alpha. A mediator of focal ischemic brain injury.* Stroke, 1997. 28(6): p. 1233-44.

Jan. 1, 1940, Batson, O.V., *The Function of the Vertebral Veins and their role in the spread of metastases.* Annals of Surgery, 1940. 112: p. 138-149.

Jan. 1, 1957, Batson, O.V., *The Vertebral Vein System, Caldwell Lecture,* 1956. American Journal of Roentgenology, 1957. 78(2).

Jan. 1, 2007, Bensouda-Grimaldi, L., et al., *Adalimumab-associated multiple sclerosis.* J Rheumatol, 2007. 34(1): p. 239-40; discussion 240.

Jan. 1, 2010, Boado, R.J., et al., *Selective targeting of a TNFR decoy receptor pharmaceutical to the primate brain as a receptor-specific IgG fusion protein.* J Biotechnol, 2010. 146(1-2): p. 84-91.

Jan. 1, 1996, Breitner, J.C., *The role of anti-inflammatory drugs in the prevention and treatment of Alzheimer's disease.* Annu Rev Med, 1996. 47: p. 401-11.

Jul. 10, 2001, Brisby, H., et al., *Proinflammatory cytokines in cerebrospinal fluid and serum in patients with disc herniation and sciatica.* Eur Spine J, 2002. 11(1): p. 62-6.

Jan. 1, 2000, Cooper, N.R., et al., *Key issues in Alzheimer's disease inflammation.* Neurobiol Aging, 2000. 21(3): p. 451-453.

Jan. 1, 1886, Corning, J.L., *Local anæsthesia in general medicine and surgery, being the practical application of the author's recent discoveries* 1886, New York,: D. Appleton and company. 103 p.

Jan. 1, 2008, Dolga, A.M., et al., *TNF-alpha-mediates neuroprotection against glutamate-induced excitotoxicity via NF-kappaB-dependent up-regulation of K2.2 channels.* J Neurochem, 2008. 107(4): p. 1158-67.

Aug. 12, 2004, Edsbagge, M., et al., *Spinal CSF absorption in healthy individuals.* Am J Physiol Regul Integr Comp Physiol, 2004. 287(6): p. R1450-5.

Jun. 1, 2006, Edwards, M.M. and S.R. Robinson, *TNF alpha affects the expression of GFAP and S100B: implications for Alzheimer's disease.* J Neural Transm, 2006. 113(11): p. 1709-15.

Jan. 1, 1999, Engelborghs, S., et al., *Unchanged levels of interleukins, neopterin, interferon-gamma and tumor necrosis factor-alpha in cerebrospinal fluid of patients with dementia of the Alzheimer type.* Neurochem Int, 1999. 34(6): p. 523-30.

Jan. 1, 2009, Esposito, E. and S. Cuzzocrea, *TNF-alpha as a therapeutic target in inflammatory diseases, ischemia-reperfusion injury and trauma.* Curr Med Chem, 2009. 16(24): p. 3152-67.

Jan. 1, 1986, Falk, D., *Evolution of cranial blood drainage in hominids: enlarged occipital/marginal sinuses and emissary foramina.* Am J Phys Anthropol, 1986. 70(3): p. 311-24.

Dec. 1, 1983, Falk, D.C., G., *The Cranial Venous Sinus System in Australopithecus afarensis.* Letters to Nature, 1983. 306(22/29): p. 779-781.

Jan. 1, 1996, Fan, L., et al., *Experimental brain injury induces differential expression of tumor necrosis factor-alpha mRNA in the CNS.* Brain Res Mol Brain Res, 1996. 36(2): p. 287-91.

Jan. 1, 1998, Feuerstein, G., X. Wang, and F.C. Barone, *Cytokines in brain ischemia—the role of TNF alpha.* Cell Mol Neurobiol, 1998. 18(6): p. 695-701.

Jan. 1, 1994, Feuerstein, G.Z., T. Liu, and F.C. Barone, *Cytokines, inflammation, and brain injury: role of tumor necrosis factor-alpha.* Cerebrovasc Brain Metab Rev, 1994. 6(4): p. 341-60.

Jan. 1, 1998, Feuerstein, G.Z., X. Wang, and F.C. Barone, *The role of cytokines in the neuropathology of stroke and neurotrauma.* Neuroimmunomodulation, 1998. 5(34): p. 143-59.

Jan. 1, 2008, Figiel, I., *Pro-inflammatory cytokine TNF-alpha as a neuroprotective agent in the brain.* Acta Neurobiol Exp (Wars), 2008. 68(4): p. 526-34.

Jan. 1, 1991, Fillit, H., et al., *Elevated circulating tumor necrosis factor levels in Alzheimer's disease.* Neurosci Lett, 1991. 129(2): p. 318-20.

Jan. 1, 2002, Fontaine, V., et al., *Neurodegenerative and neuroprotective effects of tumor Necrosis factor (TNF) in retinal ischemia: opposite roles of TNF receptor 1 and TNF receptor 2.* J Neurosci, 2002. 22(7): p. RC216.

Jan. 1, 1989, Gallo, P., et al., *Tumor necrosis factor alpha (TNF alpha) and neurological diseases. Failure in detecting TNF alpha in the cerebrospinal fluid from patients with multiple sclerosis, AIDS dementia complex, and brain tumours.* J Neuroimmunol, 1989. 23(1): p. 4-14.

Apr. 28, 2004, Genevay, S., S. Stingelin, and C. Gabay, *Efficacy of etanercept in the treatment of acute, severe sciatica: a pilot study.* Ann Rheum Dis, 2004. 63(9): p. 1120-3.

Aug. 25, 2004, Gentleman, S.M., et al., *Long-term intracerebral inflammatory response after traumatic brain injury.* Forensic Sci Int, 2004. 146(2-3): p. 97-104.

Nov. 18, 2004, Gerhard, A., et al., *Evolution of microglial activation in patients after ischemic stroke: a [11C] (R)-PK11195 PET study.* Neuroimage, 2005. 24(2): p. 591-5.

Jan. 1, 2004, Gisolf, J., et al., *Human cerebral venous outflow pathway depends on posture and central venous pressure.* J Physiol, 2004. 560(Pt 1): p. 317-27.

Sep. 1, 2004, Glabinski, A.R., et al., *Treatment with soluble tumor necrosis factor receptor (sTNFR):Fc/p80 fusion protein ameliorates relapsing-remitting experimental autoimmune encephalomyelitis and decreases chemokine expression.* Autoimmunity, 2004. 37(6-7): p. 465-71.

Oct. 11, 2007, Gomez-Gallego, M., J. Meca-Lallana, and A. Fernandez-Barreiro, *Multiple sclerosis onset during etanercept treatment.* Eur Neurol, 2008. 59(1-2): p. 91-3.

Jan. 1, 1990, Goodman, J.C., et al., *Elevation of tumor necrosis factor in head injury.* J Neuroimmunol, 1990. 30(2-3): p. 213-7.

Jan. 10, 2008, Griffin, W.S., *Perispinal etanercept: potential as an Alzheimer therapeutic.* J Neuroinflammation, 2008. 5: p. 3.

Jan. 1, 2004, Groen, R.J., et al., *Anatomical and pathological considerations in percutaneous vertebroplasty and kyphoplasty: a reappraisal of the vertebral venous system.* Spine, 2004. 29(13): p. 1465-71.

Sep. 12, 2005, Heldmann, U., et al., *TNF-alpha antibody infusion impairs survival of stroke-generated neuroblasts in adult rat brain.* Exp Neurol, 2005. 196(1): p. 204-8.

Aug. 1, 1989, Hofman, F.M., et al., *Tumor necrosis factor identified in multiple sclerosis brain.* J Exp Med, 1989. 170(2): p. 607-12.

Nov. 19, 2008, Hulse, R.E., et al., *Monomeric IgG is neuroprotective via enhancing microglial recycling endocytosis and TNF-alpha.* J Neurosci, 2008. 28(47): p. 12199-211.

Apr. 1, 2001, Ibukuro, K., et al., *Topographic anatomy of the vertebral venous system in the thoracic inlet.* AJR Am J Roentgenol, 2001. 176(4): p. 1059-65.

Jan. 1, 2004, Igarashi, A., et al., *Inflammatory cytokines released from the facet joint tissue in degenerative lumbar spinal disorders.* Spine, 2004. 29(19): p. 2091-5.

Jan. 1, 1999, Ignatowski, T.A., et al., *Brain-derived TNFalpha mediates neuropathic pain.* Brain Res, 1999. 841(1-2): p. 70-7.

(56) References Cited

OTHER PUBLICATIONS

Jan. 1, 2004, Ignatowski, T.A., et al., *The dissipation of neuropathic pain paradoxically involves the presence of tumor necrosis factor-alpha (TNF)*.

Jan. 1, 2009, Kato, K., et al., *Distribution and tumor necrosis factor-alpha isoform binding specificity of locally administered etanercept into injured and uninjured rat sciatic nerve*. Neuroscience, 2009. 160(2): p. 492-500.

Feb. 27, 2008, Kaushal, V. and L.C. Schlichter, *Mechanisms of microglia-mediated neurotoxicity in a new model of the stroke penumbra*. J Neurosci, 2008. 28(9): p. 2221-30.

Jan. 1, 1997, Klegeris, A., D.G. Walker, and P.L. McGeer, *Interaction of Alzheimer beta-amyloid peptide with the human monocytic cell line THP-1 results in a protein kinase C-dependent secretion of tumor necrosis factor-alpha*. Brain Res, 1997. 747(1): p. 114-21.

Jan. 1, 1997, Klinkert, W.E., et al., *TNF-alpha receptor fusion protein prevents experimental auto-immune encephalomyelitis and demyelination in Lewis rats: an overview*. J Neuroimmunol, 1997. 72(2): p. 163-8.

Jan. 1, 1999, Knoblach, S.M., L. Fan, and A.I. Faden, *Early neuronal expression of tumor necrosis factor-alpha after experimental brain injury contributes to neurological impairment*. J Neuroimmunol, 1999. 95(1-2): p. 115-25.

Jan. 1, 2005, Larsson, K., B. Rydevik, and K. Olmarker, *Disc related cytokines inhibit axonal outgrowth from dorsal root ganglion cells in vitro*. Spine, 2005. 30(6): p. 621-4.

Jan. 1, 2005, Laws, S.M., et al., *TNF polymorphisms in Alzheimer disease and functional implications on CSF beta-amyloid levels*. Hum Mutat, 2005. 26(1): p. 29-35.

Dec. 1, 2003, Lirk, P., et al., *Cervical and high thoracic ligamentum flavum frequently fails to fuse in the midline*. Anesthesiology, 2003. 99(6): p. 1387-90.

Jan. 1, 2004, Lirk, P., et al., *The incidence of lumbar ligamentum flavum midline gaps*. Anesth Analg, 2004. 98(4): p. 1178-80, table of contents.

Jan. 1, 1994, Liu, T., et al., *Tumor necrosis factor-alpha expression in ischemic neurons*. Stroke, 1994. 25(7): p. 1481-8.

Jan. 1, 2009, Looseley, A., *Corning and cocaine: the advent of spinal anesthesia*. Grand Rounds, 2009. 9: p. L1-L4.

Jan. 1, 1999, Mackey, D.C., *The history of spinal drug delivery: the evolution of lumbar puncture and spinal narcosis*, in *Spinal Drug Delivery*, T.L. Yaksh, Editor 1999, Elsevier: Amsterdam.

Jan. 1, 1995, Maness, L.M., et al., *Selective transport of blood-borne interleukin-1 alpha into the posterior division of the septum of the mouse brain*. Brain Res, 1995. 700(1-2): p. 83-8.

Jul. 30, 2004, Marchetti, L., et al., *Tumor necrosis factor (TNF)-mediated neuroprotection against glutamate-induced excitotoxicity is enhanced by N-methyl-D-aspartate receptor activation. Essential role of a TNF receptor 2-mediated phosphatidylinositol 3-kinase-dependent NF-kappa B pathway*. J Biol Chem, 2004. 279(31): p. 32869-81.

Jan. 1, 1992, Mastroianni, C.M., et al., *Tumour necrosis factor (TNF-alpha) and neurological disorders in HIV infection*. J Neurol Neurosurg Psychiatry, 1992. 55(3): p. 219-21.

Jan. 1, 1997, Mattson, M.P., et al., *Cellular signaling roles of TGF beta, TNF alpha and beta APP in brain injury responses and Alzheimer's disease*. Brain Res Brain Res Rev, 1997. 23(1-2): p. 47-61.

Aug. 1, 1996, McGeer, P.L., M. Schulzer, and E.G. McGeer, *Arthritis and anti-inflammatory agents as possible protective factors for Alzheimer's disease: a review of 17 epidemiologic studies*. Neurology, 1996. 47(2): p. 425-32.

May 16, 2007, Medeiros, R., et al., *Connecting TNF-alpha signaling pathways to iNOS expression in a mouse model of Alzheimer's disease: relevance for the behavioral and synaptic deficits induced by amyloid beta protein*. J Neurosci, 2007. 27(20): p. 5394-404.

Dec. 1, 2001, Mohan, N., et al., *Demyelination occurring during anti-tumor necrosis factor alpha therapy for inflammatory arthritides*. Arthritis Rheum, 2001. 44(12): p. 2862-9.

Aug. 1, 1993, Mohler, K.M., et al., *Soluble tumor necrosis factor (TNF) receptors are effective therapeutic agents in lethal endotoxemia and function simultaneously as both TNF carriers and TNF antagonists*. J Immunol, 1993. 151(3): p. 1548-61.

Jan. 1, 2006, Murata, Y., et al., *Nucleus pulposus-induced apoptosis in dorsal root ganglion following experimental disc herniation in rats*. Spine, 2006. 31(4): p. 382-90.

Jan. 1, 2008, Murata, Y., et al., *The role of tumor necrosis factor—alpha in apoptosis of dorsal root ganglion cells induced by herniated nucleus pulposus in rats*. Spine, 2008. 33(2): p. 155-62.

Jan. 1, 2006, Murata, Y., et al., *Production of tumor necrosis factor—alpha from porcine nucleus pulposus cells at various time points in cell culture under conditions of nutritional deficiency*. Cytokine, 2006. 34(3-4): p. 206-11.

Jan. 1, 2006, Murata, Y., et al., *Changes in pain behavior and histologic changes caused by application of tumor necrosis factor-alpha to the dorsal root ganglion in rats*. Spine, 2006. 31(5): p. 530-5.

Jan. 1, 2004, Murata, Y., et al., *Selective inhibition of tumor necrosis factor-alpha prevents nucleus pulposus-induced histologic changes in the dorsal root ganglion*. Spine, 2004. 29(22): p. 2477-84.

Jan. 1, 2004, Murata, Y., et al., *Distribution and appearance of tumor necrosis factor-alpha in the dorsal root ganglion exposed to experimental disc herniation in rats*. Spine, 2004. 29(20): p. 2235-41.

Jan. 1, 1999, Nadeau, S. and S. Rivest, *Effects of circulating tumor necrosis factor on the neuronal activity and expression of the genes encoding the tumor necrosis factor receptors (p55 and p75) in the rat brain: a view from the blood-brain barrier*. Neuroscience, 1999. 93(4): p. 1449-64.

Jan. 1, 1997, Nawashiro, H., D. Martin, and J.M. Hallenbeck, *Neuroprotective effects of TNF binding protein in focal cerebral ischemia*. Brain Res, 1997. 778(2): p. 265-71.

Jan. 1, 2001, Olmarker, K., *Radicular pain—recent pathophysiologic concepts and therapeutic implications*. Schmerz, 2001. 15(6): p. 425-9.

Jan. 1, 1994, Olmarker, K., et al., *Effects of methylprednisolone on nucleus pulposus-induced nerve root injury*. Spine, 1994. 19(16): p. 1803-8.

Dec. 1, 1998, Olmarker, K. and K. Larsson, *Tumor necrosis factor alpha and nucleus-pulposus-induced nerve root injury*. Spine, 1998. 23(23): p. 2538-44.

Jan. 1, 2003, Olmarker, K., M. Nutu, and R. Storkson, *Changes in spontaneous behavior in rats exposed to experimental disc herniation are blocked by selective TNF-alpha inhibition*. Spine, 2003. 28(15): p. 1635-41; discussion 1642.

Jan. 1, 2001, Olmarker, K. and B. Rydevik, *Selective inhibition of tumor necrosis factor-alpha prevents nucleus pulposus-induced thrombus formation, intraneural edema, and reduction of nerve conduction velocity: possible implications for future pharmacologic treatment strategies of sciatica*. Spine, 2001. 26(8): p. 863-9.

Jan. 1, 2004, Onda, A., et al., *Infliximab attenuates immunoreactivity of brain-derived neurotrophic factor in a rat model of herniated nucleus pulposus*. Spine, 2004. 29(17): p. 1857-61.

Jan. 1, 2000, Pappata, S., et al., *Thalamic microglial activation in ischemic stroke detected in vivo by PET and [11C]PK1195*. Neurology, 2000. 55(7): p. 1052-4.

Jan. 1, 2005, Pardridge, W.M., *The blood-brain barrier: bottleneck in brain drug development*. NeuroRx, 2005. 2(1): p. 3-14.

Jan. 1, 2001, Perry, R.T., et al., *The role of TNF and its receptors in Alzheimer's disease*. Neurobiol Aging, 2001. 22(6): p. 873-83.

Jan. 1, 2005, Pickering, M., D. Cumiskey, and J.J. O'Connor, *Actions of TNF-alpha on glutamatergic synaptic transmission in the central nervous system*. Exp Physiol, 2005. 90(5): p. 663-70.

Aug. 1, 2006, Ramos, E.M., et al., *Tumor necrosis factor alpha and interleukin 10 promoter region polymorphisms and risk of late-onset Alzheimer disease*. Arch Neurol, 2006. 63(8): p. 1165-9.

Jan. 1, 1962, Rieselbach, R.E., et al., *Subarachnoid distribution of drugs after lumbar injection*. N Engl J Med, 1962. 267: p. 1273-8.

Jan. 1, 1994, Ross, S.A., et al., *The presence of tumour necrosis factor in CSF and plasma after severe head injury*. Br J Neurosurg, 1994. 8(4): p. 419-25.

Jan. 1, 2003, Rutgeerts, P., et al., *Treatment of active Crohn's disease with onercept (recombinant human soluble p55 tumour necrosis fac-*

(56) References Cited

OTHER PUBLICATIONS tor receptor): results of a randomized, open-label, pilot study. Aliment Pharmacol Ther, 2003. 17(2): p. 185-92.
Sep. 1, 2006, Saha, R.N., X. Liu, and K. Pahan, *Up-regulation of BDNF in astrocytes by TNF-alpha: a case for the neuroprotective role of cytokine.* J Neuroimmune Pharmacol, 2006. 1(3): p. 212-22.
Oct. 1, 2002, San Millan Ruiz, D., et al., *The craniocervical venous system in relation to cerebral venous drainage.* AJNR Am J Neuroradiol, 2002. 23(9): p. 1500-8.
Jan. 1, 2003, Sharma, H.S., et al., *Topical application of TNF-alpha antiserum attenuates spinal cord trauma induced edema formation, microvascular permeability disturbances and cell injury in the rat.* Acta Neurochir Suppl, 2003. 86: p. 407-13.
Jan. 1, 2003, Sheng, J.G., et al., *Lipopolysaccharide-induced-neuroinflammation increases intracellular accumulation of amyloid precursor protein and amyloid beta peptide in APPswe transgenic mice.* Neurobiol Dis, 2003. 14(1): p. 133-45.
Jan. 1, 1999, Shinpo, K., et al., *Protective effects of the TNF-ceramide pathway against glutamate neurotoxicity on cultured mesencephalic neurons.* Brain Res, 1999. 819(1-2): p. 170-3.
Jan. 1, 1996, Shohami, E., et al., *Inhibition of tumor necrosis factor alpha (TNFalpha) activity in rat brain is associated with cerebro protection after closed head injury.* J Cereb Blood Flow Metab, 1996. 16(3): p. 378-84.
Jan. 1, 1997, Shohami, E., et al., *Cytokine production in the brain following closed head injury: dexanabinol (HU-211) is a novel TNF-alpha inhibitor and an effective neuroprotectant.* J Neuroimmunol, 1997. 72(2): p. 169-77.
Jan. 1, 1994, Shohami, E., et al., *Closed head injury triggers early production of TNF alpha and IL-6 by brain tissue.* J Cereb Blood Flow Metab, 1994. 14(4): p. 615-9.
Jan. 1, 2000, Shubayev, V.I. and R.R. Myers, *Upregulation and interaction of TNFalpha and gelatinases A and B in painful peripheral nerve injury.* Brain Res, 2000. 855(1): p. 83-9.
Jan. 1, 2001, Shubayev, V.I. and R.R. Myers, *Axonal transport of TNF-alpha in painful neuropathy: distribution of ligand tracer and TNF receptors.* J Neuroimmunol, 2001. 114(1-2): p. 48-56.
Jan. 1, 2002, Shubayev, V.I. and R.R. Myers, *Anterograde TNF alpha transport from rat dorsal root ganglion to spinal cord and injured sciatic nerve.* Neurosci Lett, 2002. 320(1-2): p. 99-101.
Jan. 1, 2002, Shubayev, V.I. and R.R. Myers, *Endoneurial remodeling by TNFalph-and TNFalpha-releasing proteases. A spatial and temporal co-localization study in painful neuropathy.* J Peripher Nery Syst, 2002. 7(1): p. 28-36.
Jan. 1, 2001, Sicotte, N.L. and R.R. Voskuhl, *Onset of multiple sclerosis associated with anti-TNF therapy.* Neurology, 2001. 57(10): p. 1885-8.
Jan. 1, 2004, Sjogren, M., et al., *Increased intrathecal inflammatory activity in frontotemporal dementia: pathophysiological implications.* J Neurol Neurosurg Psychiatry, 2004. 75(8): p. 1107-11.
Jan. 1, 2001, Sommer, C., et al., *Etanercept reduces hyperalgesia in experimental painful neuropathy.* J Peripher Nery Syst, 2001. 6(2): p. 67-72.
Jan. 1, 1996, Spuler, S., et al., *Multiple sclerosis: prospective analysis of TNF-alpha and 55 kDa TNF receptor in CSF and serum in correlation with clinical and MRI activity.* J Neuroimmunol, 1996. 66(1-2): p. 57-64.
Jan. 7, 2004, Suzuki, T., et al., *Production and release of neuroprotective tumor necrosis factor by P2X7 receptor-activated microglia.* J Neurosci, 2004. 24(1): p. 1-7.
Jan. 1, 1992, Tancredi, V., et al., *Tumor necrosis factor alters synaptic transmission in rat hippocampal slices.* Neurosci Lett, 1992. 146(2): p. 176-8.
Jul. 1, 2003, Tariot, P.N. and H.J. Federoff, *Current treatment for Alzheimer disease and future prospects.* Alzheimer Dis Assoc Disord, 2003. 17 Suppl 4: p. S105-13.
Jan. 1, 2002, Tarkowski, E., *Cytokines in dementias* Curr Drug Targets Inflamm Allergy, 2002. 1(2): p. 193-200.
Jan. 1, 2003, Tarkowski, E., et al., *Intrathecal inflammation precedes development of Alzheimer's disease.* J Neurol Neurosurg Psychiatry, 2003. 74(9): p. 1200-5.
Jul. 1, 1999, Tarkowski, E., et al., *Intracerebral production of tumor necrosis factor-alpha, a local neuroprotective agent, in Alzheimer disease and vascular dementia.* J Clin Immunol, 1999. 19(4): p. 223-30.
Jan. 1, 2003, Tarkowski, E., et al., *Cerebral pattern of pro- and anti-inflammatory cytokines in dementias.* Brain Res Bull, 2003. 61(3): p. 255-60.
Oct. 1, 1991, Tartaglia, L.A., et al., *The two different receptors for tumor necrosis factor mediate distinct cellular responses.* Proc Natl Acad Sci U S A, 1991. 88(20): p. 9292-6.
Jan. 1, 2008, Tedde, A., et al., *Lack of association between TNF-alpha polymorphisms and Alzheimer's disease in an Italian cohort.* Neurosci Lett, 2008.
Jan. 1, 2000, Terrado, J., et al., *Soluble TNF receptors partially protect injured motoneurons in the postnatal CNS.* Eur J Neurosci, 2000. 12(9): p. 3443-7.
Jan. 1, 2004, Tobinick, E., *TNF-alpha inhibition for potential therapeutic modulation of SARS coronavirus infection.* Curr Med Res Opin, 2004. 20(1): p. 39-40.
Jan. 1, 2006, Tobinick, E., *Spinal delivery of p38: TNF-alpha inhibitors.* PLoS Med, 2006. 3(11): p. e511.
Jan. 1, 2007, Tobinick, E., *Perispinal etanercept for treatment of Alzheimer's disease.* Curr Alzheimer Res, 2007. 4(5): p. 550-2.
Jun. 10, 2008, Tobinick, E., *Perispinal etanercept produces rapid improvement in primary progressive aphasia: identification of a novel, rapidly reversible TNF-mediated pathophysiologic mechanism.* Medscape J Med, 2008. 10(6): p. 135.
Feb. 1, 2009, Tobinick, E., *Perispinal etanercept for neuroinflammatory disorders.* Drug Discov Today, 2009. 14(3-4): p. 168-77.
Jan. 1, 2004, Tobinick, E. and S. Davoodifar, *Efficacy of etanercept delivered by perispinal administration for chronic back and/or neck disc-related pain: a study of clinical observations in 143 patients.* Curr Med Res Opin, 2004. 20(7): p. 1075-85.
Jan. 1, 2006, Tobinick, E., et al., *TNF-alpha modulation for treatment of Alzheimer's disease: a 6-month pilot study.* MedGenMed, 2006. 8(2): p. 25.
Feb. 22, 2006, Tobinick, E. and C.P. Vega, *The cerebrospinal venous system: anatomy, physiology, and clinical implications.* MedGenMed, 2006. 8(1): p. 53.
Jan. 1, 2003, Tobinick, E.L., *Targeted etanercept for treatment—refractory pain due to bone metastasis: two case reports.* Clin Ther, 2003. 25(8): p. 2279-88.
Jan. 1, 2003, Tobinick, E.L., *Targeted etanercept for discogenic neck pain: uncontrolled, open-label results in two adults.* Clin Ther, 2003. 25(4): p. 1211-8.
Apr. 1, 2008, Tobinick, E.L., *Re: Inflammatory markers and the risk of Alzheimer disease: the Framingham Study.* Neurology, 2008. 70(14): p. 1222-3; author reply 1223.
Feb. 1, 2008, Tobinick, E.L., *A critique of intradiscal administration for treatment of radiculopathy.* Anesthesiology, 2008. 108(2): p. 334; author reply 335.
Jan. 1, 2003, Tobinick, E.L. and S. Britschgi-Davoodifar, *Perispinal TNF-alpha inhibition for discogenic pain.* Swiss Med Wkly, 2003. 133(11-12): p. 170-7.
Jul. 21, 2008, Tobinick, E.L. and H. Gross, *Rapid improvement in verbal fluency and aphasia following perispinal etanercept in Alzheimer's disease.* BMC Neurol, 2008. 8: p. 27.
Jan. 9, 2008, Tobinick, E.L. and H. Gross, *Rapid cognitive improvement in Alzheimer's disease following perispinal etanercept administration.* J Neuroinflammation, 2008. 5: p. 2.
Jan. 4, 2006, Turrin, N.P. and S. Rivest, *Tumor necrosis factor alpha but not interleukin 1 beta mediates neuroprotection in response to acute nitric oxide excitotoxicity.* J Neurosci, 2006. 26(1): p. 143-51.
Jan. 1, 1996, van Oosten, B.W., et al., *Increased MRI activity and immune activation in two multiple sclerosis patients treated with the monoclonal anti-tumor necrosis factor antibody cA2.* Neurology, 1996. 47(6): p. 1531-4.
Jan. 1, 2006, Virna, S., et al., *TNF is important for pathogen control and limits brain damage in murine cerebral listeriosis.* J Immunol, 2006. 177(6): p. 3972-82.

(56) References Cited

OTHER PUBLICATIONS

Nov. 1, 1996, Wagner, R. and R.R. Myers, *Endoneurial injection of TNF-alpha produces neuropathic pain behaviors.* Neuroreport, 1996. 7(18): p. 2897-901.
Jan. 1, 1994, Wen, T.S., D.C. Randall, and J.F. Zolman, *Protein accumulation in cerebrospinal fluid during-90 degrees head-down tilt in rabbit.* J Appl Physiol (1985), 1994. 77(3): p. 1081-6.
Jan. 1, 2002, Wiendl, H. and R. Hohlfeld, *Therapeutic approaches in multiple sclerosis: lessons from failed and interrupted treatment trials.* BioDrugs, 2002. 16(3): p. 183-200.
Jan. 1, 2002, Wilson, C.J., C.E. Finch, and H.J. Cohen, *Cytokines and cognition—the case for a head-to-toe inflammatory paradigm.* J Am Geriatr Soc, 2002. 50(12): p. 2041-56.
Jan. 1, 2001, Zaremba, J. and J. Losy, *Early TNF-alpha levels correlate with ischaemic stroke severity.* Acta Neurol Scand, 2001. 104(5): p. 288-95.
European Search Report of related application EP 11838617.5, Feb. 21, 2014.
Heijnen C J et al: "Neuro-immune, behavioral and molecular aspects of brain damage", Brain, Behavior and Immunity, Academic Press, San Diego, CA, US, vol. 24, No. 5, Jul. 1, 2010, pp. 705-707, XP027474148, ISSN: 0889-1591, DoI: 10.1016/J.BBI.2010.01.012 [retrieved on Feb. 4, 2010] p. 706.
Ward, "Spasticity treatment with botulinum toxins," J Neural Trasm (2008) 115; 607-616.
Tobiniek et al., CNS Drugs 2012;26(12):1051-70 (Selective TNF Inhibition for Chronic Stroke and Traumatic Brain Injury—An Observational Study Involving 629 Consecutive Patients Treated with Perispinal Etanercept.
Sheeati, G., European Journal of Neurology 2002, 9 (Suppl. 1):3-9, "The pathophysiology of spasticity".
Burke, D., et al., Neurology 2013; 80 (Suppl 2);S20-S26, "Pathophysiology of spasticity in stroke".
Thibaut et al., Brain Injury, Early Online 1-13 (2013, Informa U.K. Review: "Spasticity after stroke: Physiology, assessment and treatment".
Baguley, "A Critical Review of the Pathophysiology of Dysautonomia Following Traumatic Brain Injury" Neurocrit Care (2008)8 293-300.
Ward, A.B., "A literature review of the pathophysiology and onset of post-stroke spasticity" European Journal of Neurology 2012, 19: 21-27.
Barnes, M. "Botulinum Toxin—Mechanisms of Action and Clinical Use in Spasticity" J Rehabil Med 2003; Suppl. 41: 56-59.
Gallichio, J.E., "Pharmacologic Management of Spasticity Following Stroke," Physical Therapy . vol. 84 . No. 10 . Oct. 2004.

\* cited by examiner

METHODS FOR TREATMENT OF BRAIN INJURY UTILIZING BIOLOGICS

CROSS REFERENCE TO RELATED APPLICATIONS

This application is a national stage entry of PCT/US11/58573, filed Oct. 31, 2011, which claims the benefit of U.S. provisional application No. 61/409,012, filed Nov. 1, 2010, and PCT/US11/58573, filed Oct. 31, 2011, claims the benefit of U.S. provisional application No. 61/413,440, filed Nov. 13, 2010, and PCT/US11/58573, filed Oct. 31, 2011, claims the benefit of U.S. provisional application No. 61/413,444, filed Nov. 14, 2010, which are all incorporated by reference.

FIELD OF THE INVENTION

The use of biologics for treatment of humans with brain injury and other forms of neurological injury, including injury due to stroke, thrombosis, embolus, ischemia, hemorrhage, trauma, cerebral hypoxia or anoxia, carbon monoxide poisoning, drowning, or cardiac arrest.

BACKGROUND OF THE INVENTION

Lack of adequate oxygenation of brain tissue causes brain injury. A stroke occurs when the blood supply to part of the brain is suddenly interrupted or when a blood vessel in the brain bursts, spilling blood into the spaces surrounding brain cells, or when the brain or a portion of the brain is deprived of oxygen or oxygenation is impaired by exogenous substances such as carbon monoxide, hemorrhage, or hypoperfusion. Brain cells die when they no longer receive adequate oxygen and nutrients from the blood or there is sudden bleeding into or around the brain. The symptoms of a stroke include sudden numbness or weakness, especially on one side of the body; sudden confusion or trouble speaking or understanding speech; sudden trouble seeing in one or both eyes; sudden trouble with walking, dizziness, or loss of balance or coordination; or sudden severe headache with no known cause. There are several forms of stroke, including: ischemic—blockage of a blood vessel supplying the brain, due to thrombosis or embolus, and hemorrhagic—bleeding into the brain tissue (intracerebral hemorrhage), or into the subarachnoid space (subarachnoid hemorrhage). Brain injury can also occur from subdural or epidural hematoma. Stroke involving the spinal cord can also occur due to the same or similar causes of stroke involving the brain (ischemia, hemorrhage, hypoperfusion, etc.). Traumatic brain injury (TBI), a form of acquired brain injury, occurs when a sudden trauma causes damage to the brain. TBI can result when the head suddenly and violently hits an object, or when an object pierces the skull and enters brain tissue. Symptoms of a TBI can be mild, moderate, or severe, depending on the extent of the damage to the brain. A person with a mild TBI may remain conscious or may experience a loss of consciousness for a few seconds or minutes. Other symptoms of mild TBI include headache, confusion, lightheadedness, dizziness, blurred vision or tired eyes, ringing in the ears, bad taste in the mouth, fatigue or lethargy, a change in sleep patterns, behavioral or mood changes, and trouble with memory, concentration, attention, or thinking. A person with a moderate or severe TBI may show these same symptoms, but may also have a headache that gets worse or does not go away, repeated vomiting or nausea, convulsions or seizures, an inability to awaken from sleep, dilation of one or both pupils of the eyes, slurred speech, weakness or numbness in the extremities, loss of coordination, and increased confusion, restlessness, or agitation. Adverse residual neurological and brain effects from TBI occurring years before can continue. These chronic adverse effects can include difficulties with attention, concentration, planning, calculation, reading, vision, hearing, balance and motor activities such as walking or use of hands or limbs. Traumatic brain injury can occur from repeated trauma to the head, such as occurs in contact sports such as football, boxing, or soccer, or repeated concussions of any origin.

Cerebral hypoxia refers to a condition in which there is a decrease of oxygen supply to the brain even though there is adequate blood flow. Drowning, strangling, choking, suffocation, cardiac arrest, head trauma, carbon monoxide poisoning, and complications of general anesthesia can create conditions that can lead to cerebral hypoxia. Symptoms of mild cerebral hypoxia include inattentiveness, poor judgment, memory loss, and a decrease in motor coordination. Brain cells are extremely sensitive to oxygen deprivation and can begin to die within five minutes after oxygen supply has been cut off. When hypoxia lasts for longer periods of time, it can cause coma, seizures, and even brain death. Brain injury can also occur due to radiation exposure or chemotherapy.

Spasticity is a condition in which there is an abnormal increase in muscle tone or stiffness of muscle, which might interfere with movement, speech, or be associated with discomfort or pain. Spasticity is usually caused by damage to nerve pathways within the brain or spinal cord that control muscle movement. It may occur in association with spinal cord injury, multiple sclerosis, cerebral palsy, stroke, brain or head trauma, amyotrophic lateral sclerosis, hereditary spastic paraplegias, and metabolic diseases such as adrenoleukodystrophy, phenylketonuria, and Krabbe disease. Symptoms may include hypertonicity (increased muscle tone), clonus (a series of rapid muscle contractions), exaggerated deep tendon reflexes, muscle spasms, scissoring (involuntary crossing of the legs), and fixed joints (contractures). The degree of spasticity varies from mild muscle stiffness to severe, painful, and uncontrollable muscle spasms. Spasticity can interfere with rehabilitation in patients with certain disorders, and often interferes with daily activities. (From the National Institute of Neurological Disorders and Stroke Spasticity Information webpage).

The methods of the present invention are designed to treat mammals, including humans, following stroke or other forms of neurological or brain injury (BI). Causes of BI include, but are not limited to stroke, automobile accident, anesthesia accident, near-drowning, or cerebral hemorrhage. The most common causes of BI are stroke, trauma (falls, automobile accidents, or firearm accidents); birth injuries or cerebral hypoxia. BI causes widespread, unmet medical needs, producing chronic motor deficits, spasticity, sensory deficits, cognitive deficits, deficits in attention, and alterations in mood and behavior for which current medical treatment is inadequate. Cerebral palsy is caused by brain injury prior to birth, at birth, or within the first two years of life.

Following brain injury various neuropsychiatric disorders may develop, including depression, anxiety, agitation, and post-traumatic stress disorder (PTSD). PTSD symptoms include flashbacks or bad dreams, emotional numbness, intense guilt or worry, angry outbursts, feeling "on edge," or avoiding thoughts and situations that remind them of the trauma. In PTSD, these symptoms last at least one month (National Institute of Mental Health). Traumatic events that may trigger PTSD include military combat, natural disasters, and violent crime. The methods of the present invention may be used to treat the neuropsychiatric disorders enumerated above that occur following brain injury.

Tumor necrosis factor-alpha (TNF) (the term "TNF" is equivalent to and used interchangeably herein with the term "TNF-alpha") is an endogenous molecule that modulates neuronal communication and the immune response. TNF plays a key role in the inflammatory response, in the immune response, and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other inflammatory molecules, including interleukin (IL)-6, IL-8, and IL-1; release of matrix metalloproteinases; and up-regulation of the expression of endothelial adhesion molecules, further amplifying the inflammatory and immune cascade by attracting leukocytes into extravascular tissues.

Interleukins are another group of molecules that modulate the immune response. Both TNF and interleukins are cytokines Cytokines are a group of endogenous signaling molecules. Therapeutic molecules that directly interfere with the biologic effects of cytokines (termed "cytokine antagonists", or, interchangeably "cytokine inhibitors") can be manufactured using biotechnology (e.g. recombinant DNA technology), or can be harvested from living organisms. Therapeutic molecules created by biologic processes derived from a living source are termed "biologics", in contrast to drugs that are chemically synthesized. The living sources may include humans, other animals, or microorganisms. Biologics are regulated through a specific division of the FDA. Cytokine antagonists have been developed for therapeutic human use, including biologic TNF antagonists and interleukin antagonists that take various forms, such as monoclonal antibodies, domain antibodies, antibody fragments, and fusion proteins. "TNF antagonist" and "TNF inhibitor" are terms used herein interchangeably.

Antibodies (immunoglobulins) are proteins produced by one class of lymphocytes (B cells) in response to specific exogenous foreign molecules (antigens). Monoclonal antibodies (mAb), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biological activity of that cytokine Substances which reduce the biological effect of a cytokine can be described in any of the following ways: as a cytokine blocker; as a cytokine inhibitor; or as a cytokine antagonist. In this patent, the terms "blocker", "inhibitor", and "antagonist" are used interchangeably with respect to cytokines. Domain Antibodies (dAbs) are the smallest functional binding units of antibodies, corresponding to the variable regions of either the heavy (VH) or light (VL) chains of human antibodies, and are effective cytokine antagonists. Domain antibodies are antibody fragments. Other types of antibody fragments, such as pegylated antibody fragments (e.g. certolizumab pegol) are effective cytokine antagonists.

U.S. Pat. No. 5,385,901 entitled "Method of Treating Abnormal Concentrations of TNF Alpha" discloses a method for the use of TNF antagonists. This patent does not teach the use of a biologic delivered via the vertebral venous system, as described in the present invention, for the suppression and inhibition of the action of TNF in the human body to treat disorders of the brain. U.S. Pat. No. 5,434,170 entitled "Method For Treating Neurocognitive Disorders" discloses the use of thalidomide to treat dementia. This patent does not teach the use of etanercept or another biologic delivered via the vertebral venous system to treat disorders of the brain. U.S. Pat. No. 6,277,969 discloses the use of anti-TNF antibodies for treatment of various disorders. This patent does not teach the use of etanercept or another biologic delivered via the vertebral venous system to treat disorders of the brain. U.S. Patent application 2004/0258671 by Watkins entitled "Methods for Treating Pain" discloses the use of IL-10 and IL-10 fusion protein and other biologics for treating pain. This patient application does not disclose the use of these substances to treat disorders of the brain. U.S. Pat. No. 5,656,272 to Le et al. discloses the use of TNF inhibitors for treatment of various disorders, including the use of anti-TNF monoclonal antibodies. This patent does not teach the use of etanercept or another biologic delivered via the vertebral venous system to treat disorders of the brain. U.S. Pat. No. 5,650,396 discloses a method of treating multiple sclerosis (MS) by blocking and inhibiting the action of TNF in a patient. This patent does not teach the use of etanercept or another biologic delivered via the vertebral venous system to treat disorders of the brain. U.S. Pat. No. 5,605,690 discloses the use of TNF inhibitors for treatment of various disorders. This patent does not teach the use of etanercept or another biologic delivered via the vertebral venous system to treat disorders of the brain. U.S. published application US 2003/0148955 to Pluenneke discusses etanercept treatment for dozens of clinical disorders, but it does not discuss treatment of brain injury, perispinal administration, use of the vertebral venous system, Trendelenburg positioning, nor other aspects of the current invention. U.S. Pat. Nos. 7,115,557, 6,649,589 and 6,635,250 and related applications, to Olmarker and Rydevik, and previous publications by Olmarker (see References) discuss the use of TNF inhibitors for the treatment of nerve root injury and related disorders. These patents do not teach the use of etanercept or another biologic delivered via the vertebral venous system as described in the present invention to treat disorders of the brain, and are not enabling with respect to etanercept, certolizumab pegol, and other molecules discussed herein. U.S. Pat. No. 5,863,769 discloses using IL-1 RA for treating various diseases. This patent does not teach the use of an interleukin antagonist or other biologic delivered via the vertebral venous system to treat disorders of the brain. U.S. Pat. No. 6,013,253 discloses using interferon and IL-1 RA for treating multiple sclerosis. This patent does not teach the use of an interleukin antagonist or other biologic delivered via the vertebral venous system to treat disorders of the brain. U.S. Pat. No. 5,075,222 discloses the use of IL-1 inhibitors for treatment of various disorders. This prior art patent does not teach the use of an interleukin antagonist or other biologic delivered via the vertebral venous system to treat disorders of the brain. U.S. Pat. No. 6,159,460 discloses the use of IL-1 inhibitors for the treatment of various disorders. This prior art patent does not teach the use of an interleukin antagonist or other biologic delivered via the vertebral venous system to treat disorders of the brain. U.S. Pat. No. 6,096,728 discloses the use of IL-1 inhibitors for treatment of various disorders. This prior art patent does not teach the use of an interleukin antagonist or other biologic delivered via the vertebral venous system to treat disorders of the brain.

Clemens (Clemens H J. *Die Venensysteme der menschlichen Wirbsèaule; Morphologie und funktionelle Bedeutung (De Gruyter, Berlin,* 1961) demonstrated that the internal and external vertebral venous plexuses freely intercommunicate. But Clemens did not discuss the use of the vertebral venous system (VVS) to facilitate delivery of large molecules to the brain, nor did he discuss the use of the VVS for therapeutic purposes. Groen (Groen R J, Groenewegen H J, van Alphen H A, Hoogland P V. Morphology of the human internal vertebral venous plexus: a cadaver study after intravenous Araldite CY 221 injection. *Anat Rec,* 249(2), 285-294 (1997) confirmed the fact that all three divisions of the VVS (internal and external plexuses, and the basivertebral veins) freely intercommunicated, and that all divisions of this system lacked valves. But Groen did not discuss the use of the VVS to facilitate delivery of large molecules to the brain, nor did he discuss the use of the VVS for therapeutic purposes. Batson in 1940 (Batson O V. The Function of the Vertebral Veins and their role in the spread of metastases. *Annals of Surgery,* 112, 138-149) published information regarding the vertebral venous system. Experimentally he demonstrated a connection between the pelvic venous system and the vertebral venous system, and proposed that this was a route whereby carcinoma originating in the pelvis could metastasize to the spine. His work did not propose the use of the VVS for therapeutic purposes, nor did it discuss or imply this possibility. His work did not suggest delivery of biologics to the brain. Gisolf (Gisolf J, van Lieshout J J, van Heusden K, Pott F, Stok W J, Karemaker J M. Human cerebral venous outflow pathway depends on posture and central venous pressure. *J Physiol,* 560(Pt 1), 317-327 (2004)) discussed the vertebral venous system and its connections to the cranial venous system, but did not discuss the potential use of this system as a route of administration of biologics to the brain. Retrograde cerebral perfusion has been previously demonstrated to deliver dye to the surface of the brain in pigs after superior vena caval injection (Ye J, Yang L, Del Bigio, et. al. Retrograde cerebral perfusion provides limited distribution of blood flow to the brain: a study in pigs. J Thorac Cardiovasc Surg. 1997 October; 114 (4):660-5) but the authors did not propose the use of this route to deliver biologics to the brain. Groen (Groen R, du Toit D, Phillips F, et. al. Anatomical and Pathological Considerations in Percutaneous Vertebroplasty and Kyphoplasty: A reappraisal of the vertebral venous system. Spine 29(13): 1465-1471 (2004)) discussed the anatomy and function of the vertebral venous system but did not propose the use of the vertebral venous system as a route of delivery of biologics to the brain. Byrod discussed a mechanism whereby substances applied epidurally can cross into the endoneurial space (Byrod G, Rydevik B, Johansson B R, Olmarker K. Transport of epidurally applied horseradish peroxidase to the endoneurial space of dorsal root ganglia: a light and electron microscopic study. *J Peripher Nerv Syst,* 5(4), 218-226 (2000)), but does not discuss the perispinal use of a biologic for delivery to the brain. Robinson (Robinson W H, Genovese M C, Moreland L W. Demyelinating and neurologic events reported in association with tumor necrosis factor alpha antagonism: by what mechanisms could tumor necrosis factor alpha antagonists improve rheumatoid arthritis but exacerbate multiple sclerosis? *Arthritis Rheum,* 44(9), 1977-1983 (2001)) states the prevailing view that systemic administration of etanercept does not lead to therapeutic concentrations of etanercept in the brain, because systemically administered etanercept does not cross the blood-brain barrier (BBB). Olmarker has filed applications regarding the use of anti-TNF molecules for treatment of spinal disorders, including US20010027175, 20010055594, 20030176332, 20050220791, 20010027199, and 20030039651, which have led to U.S. Pat. Nos. 6,635,250, 6,649,589, and 7,115,557 and others. None of these documents teaches perispinal administration of a biologic for delivery to the brain.

The in vivo distribution of radiolabeled etanercept delivered by perispinal etanercept in a mammal has been investigated. Perispinal administration resulted in more selective delivery of etanercept into the cerebrospinal fluid within the cerebral ventricles than did systemic (ventral tail vein) administration. See Tobinick E., Perispinal etanercept: a new therapeutic paradigm in neurology. *Expert Rev Neurother,* 10(6), 985-1002 (2010).

Methods

Animal studies were conducted in accordance with the applicable protocols by the Stanford Animal Care Committee. Etanercept (Immmunex, Amgen) was commercially purchased in powder form. Preparation of 64Cu-DOTA (1,4,7, 10-tetraazadodecane-N,N',N'',N'''-tetraacetic acid (DOTA)-etanercept was as previously described (Cao Q, Cai W, Li Z B et al. PET imaging of acute and chronic inflammation in living mice. *Eur J Nucl Med Mol Imaging,* 34(11), 1832-1842 (2007)). 150 microliters of 64Cu-DOTA-etanercept solution (ca. 1 mCi) was injected overlying the cervical spine of a 250 g Sprague-Dawley rat at the C 6-7 level using a 30 gauge needle at a depth of 6 mm while the rat was anesthetized with 2.5% isoflurane inhalation anesthesia. The rat was then placed in the head down position by tail suspension for three minutes, immediately followed by placement horizontally in the bed of a microPET imaging scanner (microPET R4 rodent model scanner, Siemens Medical Solutions USA, Inc.) designed for 5-min static scans; the scan was initiated two minutes after placement in the scanner bed and was performed from five to ten minutes after etanercept administration. The rationale for this method of peripheral administration is to deliver etanercept into the cerebrospinal venous system. The images were reconstructed by a 2-dimensional ordered-subsets expectation maximum (OSEM) algorithm, and no correction was necessary for attenuation or scatter correction.

Results

MicroPET imaging revealed accumulation of 64Cu-DOTA etanercept within the lateral and third cerebral ventricles within minutes of peripheral perispinal administration, with concentration within the choroid plexus and into the CSF suggested by the microPET images.

PET (Positron Emission Tomographic) image, transverse section, of a living rat brain following perispinal extrathecal administration of 64Cu-DOTA-etanercept, imaged 5 to 10 minutes following etanercept administration, gave a pattern consistent with penetration of 64Cu-DOTA-etanercept into the cerebrospinal fluid in the lateral and third ventricles. A horizontal linear enhancement within the lateral ventricles was noted, which is suggestive of accumulation of tracer within the choroid plexus.

The prior art fails to disclose or teach the use of perispinal administration without direct intrathecal or epidural injection of biologics, as a way of treating brain injury where said biologic is delivered via the vertebral venous system, and provides the patient with a better opportunity to heal, slows disease progression, improves brain function or otherwise improves the patient's health.

SUMMARY OF THE INVENTION

An object of the present invention to provide a method for treating a mammal having brain injury with a cytokine antagonist. Another object is to administer macromolecules via the vertebral venous system for providing suppression or inhibition of specific cytokines in a human, to improve neurological function following BI. Another object is to administer a biologic into the perispinal area, outside of the intrathecal space, via the CSVS, to improve neurological function following BI. Another object is to provide a biologic delivered via the vertebral venous system so that it reaches the brain, retina, cranial nerves, or auditory apparatus in a therapeutically effective dose and thereby improves neurological function following BI. Another object is to provide macromolecules which produce biological effects by inhibiting the inflammatory cascade in the human body for the immediate, short term (acute conditions) and long term (chronic conditions), such that these biological effects will produce clinical improvement in the patient and will give the patient a better opportunity to heal or otherwise improve neurological function following BI. Another object of the invention is to provide novel and improved routes of administration for the selected TNF antagonist so that it enters the CSVS in a therapeutically effective amount for the treatment of a human following BI, such that the use of such antagonist by this method results in delay of disease progression in a manner that is both safe, effective, and economical. Another object is to provide novel and improved routes of administration for the selected biologic so that it enters the CSVS in a therapeutically effective amount for the treatment of a human following BI such that the use of this biologic with this method results in improved health in a manner that is both safe, effective, and economical. Accordingly, it is an object of the present invention to provide an anti-TNF biologic administered through the perispinal route as a new method so that the use of the anti-TNF biologic will improve neurological function following BI. Another object of the present invention is to provide a method to deliver etanercept across the blood-brain barrier so that it is delivered to the brain in a therapeutically effective dose and thereby improve neurological function following BI.

Accordingly, it is an object of the present invention to provide a biologic administered through the perispinal route as a new method of use of such molecules so that the use of these molecules will improve neurological function following BI. Another object of the present invention is to provide a method to deliver an anti-TNF biologic so that it is delivered to the brain or the cerebrospinal fluid in a therapeutically effective dose and thereby improve neurological function following BI. Another object is to provide inhibitors of p38 MAP kinase, inhibitors of spleen tyrosine kinase, and inhibitors of Jak3 kinase, for treatment of a mammal following BI.

ABBREVIATIONS FOR FIGS. 3A, B, AND C

Figure 1:
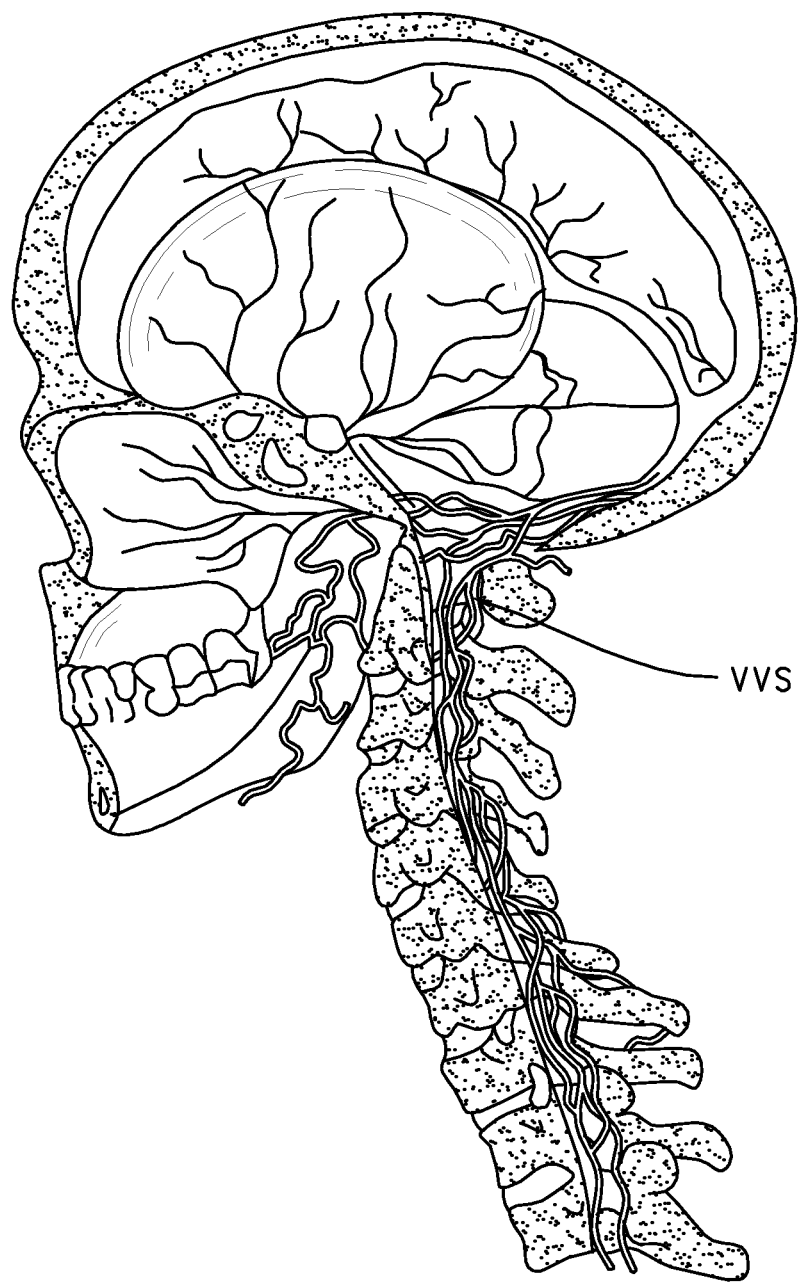
FIG. 1 is a drawing depicting a view from the side of a cross-section of the brain and the spine, showing the location and anatomic distribution of the vertebral venous system (VVS) and its continuity with the cerebral venous system.

A.C.V.—Anterior Central Vein
A.E.S.V.—Anterior External Spinal Veins
A.E,V.P.—Anterior Externol Vertebral Plexus
A.I.V.P.—Anterior Internal Vertebral Plexus
A.R.V.—Anterior Radicular Vein
B.V.V.—Basivertebral Vein
I.S.V.—Internal Spinal Veins
I.V.V.—Intervertebral Vein
P.C.V.—Posterior Centrol Vein
P.E.S.V.—Posterior External Spinal Vein
P.E.V.P.—Posterior External Vertebral Plexus
P.I.V.P.—Posterior Internal Vertebral Plexus
P.R.V.—Posterior Radicular Vein

DETAILED DESCRIPTION OF THE PREFERRED EMBODIMENTS

The insult to the brain from each of the mechanisms enumerated (including hypoxia, acute deprivation of blood flow, radiation, chemotherapy and trauma, etc.) produces an inflammatory response that results in chronic glial activation and chronic overproduction of inflammatory cytokines, including TNF. These consequences of brain injury may result in chronic neurological and neuropsychological deficits. For the purposes of this patent neurological deficits lasting three months or longer after the acute brain injury (trauma, stroke, etc.) are considered chronic, and are defined as "chronic brain injury." Chronic sequelae of brain injury includes patients who remain comatose or semi-comatose for prolonged periods of time.

This invention concerns the use of biologics for treatment of humans and other mammals following brain injury (BI), including treatment of chronic brain injury. The experimental data developed by the inventor has demonstrated, surprisingly, that the methods of the current invention may successfully treat mammals that have suffered brain injury in the remote past, i.e. months or years after the acute event. Preferred embodiments of the present invention include treatment of a human or other mammal long after initial healing from the acute event, such as more than three months, more than six months, more than one year, more than eighteen months, more than two years, more than three years or more than four years after the acute event. The methods of the present invention may also be used to treat sub-acute brain injury in the time period of two weeks to three months after the acute event. Sub-acute brain injury includes patients who are comatose or semi-comatose. The methods of the present invention may be used to treat acute brain injury in the time period of less than two weeks after the acute event.

The methods of the present invention to treat brain injury are to be considered distinct from methods to treat well-known and characterized neurodegenerative diseases, such as Parkinson's disease, Huntington's disease, Creutzfeld-Jacob disease, Alzheimer's disease, Frontotemporal dementia, Lewy Body disease, amyotrophic lateral sclerosis, etc. The methods of the present invention are designed to treat a mammal that has suffered brain injury that has generally been the result of discrete events (including single discrete events, such as an automobile accident, drowning, cardiac arrest, etc.), although a minority of humans will have suffered multiple discrete events, such as multiple concussions or multiple infusions of chemotherapy).

The methods of the present invention have repeatedly and consistently produced unprecedented clinical results which are unexplained by established physiology. In other words, the clinical results produced by the methods of the present invention establish the presence of pathophysiologic mechanisms whose existence was previously unknown. These unexpected results include, but are not limited to, not only the rapid clinical response, beginning within minutes, but also the fact that there was any clinical response at all after such long intervals after the acute brain injury.

For example, the standard concepts regarding stroke are that it is a condition that occurs suddenly due to interruption of blood supply to an area of the brain, causing damage to the brain within minutes, with rapid death of brain cells (acute stroke). Less commonly a stroke can continue to worsen over a period of hours to a day or two as a steadily enlarging area of the brain dies ("stroke in evolution"). Once the neurological deficits remain stable, normally within hours or at most a day or two, the stroke is considered completed ("completed stroke"). The inventor's concept that a completed and neurologically stable deficit, static for months or years, can be reversed, even partially, is a significant departure from standard medical and scientific conceptions. The inventor's concepts, proven by the clinical results produced by the methods of the present invention, that one can successfully intervene months or years after the acute event is a radical and unexpected departure from the existing paradigms of the brain research and medical community. A person of ordinary skill in the art would not choose the methods of the present invention and, moreover, would not even think to consider their use at such a lengthy interval after the injury. A person of ordinary skill in the art would consider neurological damage that remained fixed for two years or more following an acute brain injury (due to a stroke, etc.) to be permanent and irreversible.

Reversal of static neurological deficits beginning within minutes as a result of a single perispinal extrathecal injection of a biologic (a TNF antagonist, an interleukin antagonist, etc.) external to the ligamentum flavum, performed years after an acute brain injury, would be considered to be an impossible result by a person of ordinary skill in the art.

The methods of treatment of mammals following BI herein utilize a variety of biologics, including, but not limited to biologic TNF antagonists; biologic antagonists of inflammatory interleukins, such as IL-1 (including, but not limited to, anakinra (Kineret®, (Biovitrum) and IL-1 Trap), IL-6, and IL-12 antagonists; GM-CSF; EPO; immune globulin (including intravenous immune globulin (IVIG, such as Gammagard®)); and other biologics. TNF antagonists used in the present invention include, but are not limited to, TNF receptor fusion proteins such as etanercept and biosimilar or "biobetter" versions of etanercept, or those based upon etanercept; chimeric TNF monoclonal antibodies (mAb) such as infliximab; fully human TNF mAbs such as adalimumab and golimumab; TNF mAb fragments, such as certolizumab pegol; domain TNF antibodies; anti-TNF nanobodies; humanized TNF mAbs or mAb fragments, etc. Methods of administration include, but are not limited to, parenteral, perispinal, epidural, transepidermal, intranasal, intravenous and intramuscular routes. These methods include perispinal administration of a biologic without direct intrathecal injection. Perispinal administration is defined as administration into the anatomic area within 10 cm. of the spine. Perispinal administration results in absorption into the CSVS. In preferred embodiments, the method utilizes the CSVS to transport biologics to the brain and into the cerebrospinal fluid via retrograde venous flow, thereby bypassing the blood-brain barrier.

In addition, this invention includes the oral, topical, intranasal, perispinal, or parenteral use of inhibitors of p38 MAP kinase, inhibitors of spleen tyrosine kinase, and inhibitors of Jak3 kinase to treat BI.

In addition to human use, these methods may be used to treat other mammals, including horses, dogs, and cats with conditions analagous to BI in humans.

One preferred embodiment is the perispinal extrathecal administration of etanercept, or a biosimilar or biobetter form of etanercept, for the treatment of a human or other mammal following stroke or other forms of BI. This invention also includes other preferred embodiments, including but not limited to other methods of administration of etanercept to a human with BI, including but not limited to parenteral, subcutaneous, intravenous, transepidermal, and intranasal. Additionally this invention includes the parenteral, transepidermal or intranasal use of other TNF antagonists to treat BI. These TNF antagonists include, but are not limited to: TNF receptor fusion proteins, modified soluble TNF receptors, soluble TNF receptor constructs, TNF monoclonal antibodies (mAbs), humanized TNF mAbs, fully human TNF mAbs, chimeric TNF mAbs, domain TNF antibodies, anti-TNF nanobodies (including, but not limited to, ATN-103 and PF-05230905, Ablynx and Pfizer), mAB fragments, dominant negative TNF constructs and TNF inhibitory single chain antibody fragments. The use of catheters, pumps, or depot formulations are included as methods of the present invention.

A preferred embodiment is the perispinal extrathecal administration of etanercept, or a biosimilar or biobetter form thereof, for the treatment of spasticity due to brain injury.

One preferred embodiment is the perispinal extrathecal administration of etanercept, or a biosimilar or biobetter form, for the treatment of spasticity due to spinal cord injury.

Biologic inhibitors of the cytokine tumor necrosis factor (TNF) can be divided into two broad categories: monoclonal antibodies and their derivatives; and TNF antagonists which are not antibody-based. In the category of monoclonal antibodies and their derivatives belong golimumab, infliximab, adalimumab, certolizumab pegol, and domain antibodies against TNF, such as CEP-37247(Cephalon); and biosimilars and "biobetters" of these molecules. The category of non-antibody TNF antagonists includes, but is not limited to etanercept, pegylated soluble TNF receptor type 1 (Amgen) and biosimilars and "biobetters" of these molecules. Etanercept has a serum half life of approximately 4.8 days when administered to patients with rheumatoid arthritis on a chronic basis. Of the FDA-approved TNF antagonists, etanercept is unique because, in addition to being a TNF antagonist, etanercept also binds and antagonizes the effect of another cytokine, lymphotoxin. Lymphotoxin is a pro-inflammatory cytokine that is an immune modulator.

Perispinal administration of etanercept, or another suitable biologic, may be performed more than one time, separated by intervals of day(s), week(s), or month(s). A preferred embodiment is two doses, separated by an interval of two weeks or one month; or three doses each separated by an interval of two weeks to one month; or monthly dosing.

A preferred embodiment includes Trendelenburg positioning following perispinal administration. However perispinal administration without Trendelenburg positioning is also effective.

Advances in biotechnology have resulted in improved molecules as compared to simply using monoclonal antibodies. One such molecule is certolizumab pegol which, rather than being a monoclonal antibody is a new type of molecule, that being an antibody fragment. By removing part of the antibody structure, the function of this molecule is changed so that it acts differently in the human body. Another new type of molecule, distinct from monoclonal antibodies and soluble receptors, is a fusion protein. One such example is etanercept. This molecule has a distinct function which acts differently in the human body than a simple soluble receptor or receptors.

Cytokine antagonists can take several forms. They may be monoclonal antibodies or monoclonal antibody fragments. They may also take the form of a molecule derived from a soluble receptor to a cytokine, e.g., pegylated soluble TNF receptor type 1. Endogenous soluble cytokine receptors circulate freely in the body. When they encounter their target cytokine they bind to it, effectively inactivating the cytokine, since the cytokine is then no longer able to bind with its biologic target in the body. However, these endogenous molecules are not generally useful as therapeutics without modification, because the half-life is too short. For instance, a potent antagonist consists of two soluble receptors fused together to a specific portion of an immunoglobulin molecule (Fc fragment). This produces a dimer composed of two soluble receptors which has a high affinity for the target, and a prolonged half-life. This kind of molecule is called a fusion protein. An example of such a fusion protein is etanercept (Enbrel®).

Golimumab (Simponi®, Centocor) has been FDA-approved for treatment of rheumatoid arthritis. It may be described as a immunoglobulin G1, anti-(human tumor necrosis factor α) (human monoclonal CNTO 148γl-chain), disulfide with human monoclonal CNTO 148 κ-chain), dimer, and has CAS Registry number 476181-74-5. It is a fully human anti-TNF monoclonal antibody.

Etanercept (Enbrel®, Amgen/Immunex), golimumab, infliximab (Remicade®, Centocor), adalimumab (Humira®, Abbott), and certolizumab pegol (Cimzia®, UCB) are potent and selective inhibitors of TNF. Etanercept, adalimumab, golimumab, certolizumab pegol and infliximab are FDA approved for chronic systemic use to treat rheumatoid arthritis and certain other chronic inflammatory disorders. Etanercept has a molecular weight of approximately 150,000 daltons. Etanercept is a dimeric fusion protein consisting of two soluble TNF receptors fused to a Fc portion of an immunoglobulin molecule. This fusion protein functions in a manner quite distinct from a simple soluble TNF receptor. Soluble TNF receptors are normally present in the human body. But the use of these soluble TNF receptors as therapeutic agents for the treatment of the conditions of consideration in this patent is made impractical by their extremely short half-life and therefore their limited biologic activity. The present invention utilizing etanercept is therefore distinguished from the use of an endogenous soluble TNF receptor. It is incorrect and imprecise to describe etanercept as a soluble TNF receptor in view of its complex structure and omits characteristics of etanercept which are essential to its function. This is further underscored by the developmental history of etanercept. In its first iteration the precursor molecule to etanercept was produced with a single TNF receptor fused to an immunoglobulin fragment. The biologic activity of this molecule was poor. Therefore not only is etanercept distinguished from an endogenous soluble TNF receptor, it is also distinguished from a TNF-binding fusion protein which contains the recombinant DNA sequence of only a single soluble TNF receptor. The unique structure of etanercept, containing a dimer (two) soluble TNF receptors fused to an Fc portion of an immunoglobulin molecule, is necessary for the proper performance of one embodiment of the present invention. Since etanercept has the molecular structure of a fusion protein it is quite distinct from soluble TNF receptor type 1. However, use of pegylated soluble TNF receptor type 1 to treat BI is also an embodiment of the present invention. Unmodified endogenous soluble TNF receptors are not suitable as therapeutic agents because their half-lives are too short, on the order of seconds. Biosimilar or "biobetter" versions of etanercept are in clinical development; their use as a substitute for etanercept is a method of the present invention.

Physiologic barriers which separate the brain from the blood include the so-called "blood-brain barrier" (BBB) and the "blood-cerebrospinal fluid barrier" (BCSFB). These barriers consist of a layers of cells that comprise the cerebral capillary endothelium (the BBB), and the choroid plexus epithelium (the BCSFB). These cellular barriers contain cells that are connected by tight junctions (zonulae occludens) that may be 100 times tighter than junctions of other capillary endothelium. These tight junctions prevent molecules larger than about 600 daltons in molecular weight (MW) from traversing the BBB when the molecule is administered systemically i.e. by conventional subcutaneous, intramuscular, or intravenous injection at an anatomic site remote from the spine.

The vertebral venous system (VVS) is an interconnected plexus of veins which surrounds the spinal cord and extends the entire length of the spine. This venous system provides a vascular route from the pelvis to the cranium that is functionally distinct from the systemic venous system. First described by Willis in 1663, the functional significance of the vertebral venous system was largely unappreciated until the work of Batson, who in 1940 proposed that this venous plexus provided the route by which prostate cancer metastasizes to the vertebral column. The spinal vertebral venous system has been termed Batson's Plexus. Because of their anatomic and functional continuity, the veins, venous sinuses, and venous plexuses of the brain and spine taken together are termed the CSVS.

Perispinal administration involves anatomically localized delivery performed so as to place the therapeutic molecule directly in the vicinity of the spine at the time of initial administration. For the purposes of this patent, "in the vicinity of" is defined as within 10 centimeters of. Perispinal administration includes, but is not limited to, the following types of administration within 10 cm of the spine: parenteral; subcutaneous; intramuscular; epidural; transforaminal epidural; interlaminar; or interspinous; and specifically includes the use of interspinous injection carried through the skin in the midline of the neck or back, directly overlying the spine. For the purposes of this patent perispinal administration excludes intrathecal administration, which carries additional risks of infection and hemorrhage. Therefore in this patent "perispinal" is more exactly defined as "perispinal (extrathecal)", but for the purposes of brevity shall be designated throughout simply as "perispinal". Perispinal administration leads to enhanced delivery of large molecules to the brain and the head and the structures therein in a therapeutically effective amount. The conventional systemic modes of delivery of these molecules for clinical applications (e.g. subcutaneous administration in the abdomen, thighs, or arms; intravenous; or intramuscular) result in greatly reduced CSF delivery and all of the aforementioned systemic modes of administration are therefore distinguished from the perispinal methods of administration described in this invention. Perispinal administration superficial to the ligamentum flavum is distinguished from epidural administration, as epidural administration requires penetration of the ligamentum flavum.

Perispinal administration superficial to the ligamentum flavum results in delivery of the therapeutic molecule into the external vertebral venous plexus and subsequent delivery into the intracerebral portions of the cerebrospinal venous system.

This application concerns methods of use of biologics for effective treatment of BI. In one preferred embodiment, these methods involve perispinal administration of a biologic without direct intrathecal injection. Perispinal administration is defined as administration of the molecule into the anatomic area within 10 cm of the spine.

The methods of the present invention may utilize a wide variety of biologics, including, but not limited to, monoclonal antibodies, fusion proteins, monoclonal antibody fragments, hormones, cytokines, and anti-cytokines. In addition to the use of TNF antagonists, this invention includes the use of antagonists of other inflammatory cytokines, such as antagonists to inflammatory interleukins. Inflammatory interleukins include, but are not limited to, interleukins 1, 6 and 12. In addition to human use, these methods may be used to treat other mammals, including horses, dogs, and cats with conditions analagous to BI in humans.

Preferred embodiments include, but are not limited to, the perispinal administration of TNF antagonists for treatment of BI. Preferred embodiments include but are not limited to the use of etanercept, infliximab, adalimumab, certolizumab pegol, and golimumab. Preferred embodiments include but are not limited to the use of TNF receptor fusion proteins, modified soluble TNF receptors, soluble TNF receptor constructs, TNF mAbs, humanized TNF mAbs, anti-TNF nanobodies (including, but not limited to, ATN-103 and PF-05230905, Ablynx and Pfizer), fully human TNF mAbs, chimeric TNF mAbs, domain TNF antibodies, mAB fragments, dominant negative TNF constructs (including, but not limited to Xpro 1595(Xencor)), and TNF inhibitory single chain antibody fragments (including, but not limited to ESBA105). Preferred perispinal embodiments include, but are not limited to, epidural, transforaminal, interlaminar, and interspinous methods of administration, by injection or by catheter. Perispinal administration followed by Trendelenburg positioning, or by other forms of positioning of the body so that the head is maintained below horizontal following administration are additions to the preferred embodiments.

One preferred embodiment is the perispinal extrathecal administration of etanercept for the treatment of PTSD. This invention also includes other preferred embodiments, including but not limited to other methods of administration of etanercept to a human with PTSD, including but not limited to parenteral, subcutaneous, intravenous, transepidermal, and intranasal. Additionally this invention includes the parenteral, transepidermal or intranasal use of other TNF antagonists to treat PTSD. These TNF antagonists include, but are not limited to: TNF receptor fusion proteins, modified soluble TNF receptors, soluble TNF receptor constructs, TNF monoclonal antibodies (mAbs), humanized TNF mAbs, fully human TNF mAbs, chimeric TNF mAbs, domain TNF antibodies, mAB fragments, dominant negative TNF constructs and TNF inhibitory single chain antibody fragments. The use of catheters, pumps, or depot formulations are included as methods of the present invention.

Utilization of the vertebral venous system to deliver a biologic into the cerebral venous system is one of the preferred embodiments. "Cerebrospinal Venous System" (CSVS) is a term coined by the inventor in 2006 to describe the confluence of the spinal and cerebral venous systems because of their functional and anatomic continuity. Utilization of the CSVS to deliver a biologic into the cerebrospinal fluid or the brain or spinal cord is a preferred embodiment of the present invention.

Perispinal administration of a molecule when compared to systemic administration carries with it one or more of the following advantages for the present invention:

1) greatly improved efficacy due to improved delivery of the therapeutic molecule to the brain or the cerebrospinal fluid.

2) greater efficacy due to the achievement of higher local concentration in the interspinous space, leading to improved delivery to the VVS and the brain, and cerebrospinal fluid.
3) greater efficacy due to the ability of the administered therapeutic molecule to reach the brain and cerebrospinal fluid, without degradation caused by hepatic or systemic circulation;
4) more rapid onset of action;
5) longer duration of action; and
6) Potentially fewer side effects, due to lower required dosage.

The VVS consists of an interconnected and richly anastomosed system of veins which run along the entire length of the vertebral canal. The vertebral venous plexus, for descriptive purposes, has been separated into three intercommunicating divisions: the internal vertebral venous plexuses (anterior and posterior) lying within the spinal canal, but external to the dura; the external vertebral venous plexuses (anterior and posterior) which surround the vertebral column; and the basivertebral veins which run horizontally within the vertebrae (see accompanying FIGS. 1, 2, 2A, 3A, 3B, and 3C). Both the internal and external vertebral venous plexus course longitudinally along the entire length of the spine, from the sacrum to the cranial vault. Perispinal administration of a large molecule will result in efficient delivery of the large molecule to the VVS, with only a small amount of delivery of the large molecule into the caval venous system. Delivery of the same large molecule by intravenous infusion into an arm vein, for example, will deliver the large molecule to the caval venous system, expose the large molecule to dilution throughout the body, and fail to deliver the large molecule to the brain, cerebrospinal fluid, or the head as efficiently as perispinal administration.

The VVS may be used to introduce a variety of therapeutic molecules to the brain, retina, cranial nerves, and head via retrograde venous flow from the VVS into the cranial venous sinuses and the intracranial venous system. This method bypasses the well known barrier which prevents large molecules introduced into the systemic circulation from efficiently reaching the brain (the BBB). The BBB prevents molecules larger than approximately 600 daltons from entering the brain via the systemic circulation. Virtually all biopharmaceuticals are larger than this. For example, etanercept has a molecular weight of 149,000 daltons, and insulin has a MW of 5,000 (compared with water which has a MW of 18). This method is particularly useful, therefore, for the administration of macro-molecules (MW larger than 600 daltons), such as etanercept, TNF monoclonal antibodies, etc., whose size when delivered systemically prevents their efficient passage into the brain, but whose potency, because of their biologic origin, is extremely high. Effective delivery of these molecules to the brain using the methods of the present invention thereby enables treatment of BI.

The vertebral venous system is both anatomically and physiologically distinct from the venous system which drains the abdomen and thorax, which has been designated by others as the intracavitary (caval) venous system, with the vertebral venous system designated as the extracavitary venous system.

The methods of the present invention, in several preferred embodiments, include the perispinal administration of the biologics of consideration herein which can be accomplished in various ways, including transcutaneous interspinous injection, or catheter delivery into the epidural or interspinous space, which results in the biologics being delivered into the VVS and thence into the brain, retina, cranial nerves, spinal cord and auditory apparatus in a therapeutic amount.

This invention, in several preferred embodiments, involves the use of biologics delivered via the vertebral venous system either alone, as monotherapy, or combined with the use of other therapeutics delivered orally or otherwise for treatment of the conditions of consideration herein.

Perispinal extrathecal administration is distinguished from intrathecal administration because extrathecal administration is both safer (no dural puncture, therefore no risk of CSF leak; less risk of hemorrhage; no risk of spinal cord traumatic injury; less risk of hemorrhage and infection) and is more effective at delivering the therapeutic molecule into the VVS. The dural barrier, once crossed, will contain the therapeutic molecule within the CSF. CSF flow from the spinal cord to the brain is slow. In contrast retrograde flow to the brain via the CSVS is much more rapid.

Perispinal administration may be used to deliver biologics other than TNF antagonists to the brain and cerebrospinal fluid. These biologics include cytokine antagonists, and growth factors which affect neuronal function, or the immune response impacting neuronal function, including, but not limited to: interleukin 1 antagonists, such as IL-1 RA (Kineret®, Amgen) and IL-1 Trap; fusion proteins; BDNF; erythropoietin; GM-CSF; NGF, or other compounds with central nervous system (CNS), vascular or immune therapeutic activity. Perispinal delivery is particularly advantageous when biologics, such as etanercept, which profoundly affect neuronal function, are administered because of their efficacy at extremely low concentration (high biologic potency).

Localized administration for the treatment of brain disorders has many clinical advantages over the use of conventional systemic treatment. Local administration of a biologic results in its diffusion through local capillary, venous, arterial, and lymphatic action to reach the therapeutic target. In addition local administration of a macromolecule in the vicinity of the spine (perispinal administration) without direct intrathecal injection has the key advantage of improved delivery of the molecule to the brain via the cerebrospinal fluid (CSF), thereby bypassing the blood-brain barrier (BBB). Delivery into the CSF is enhanced by transport via the CSVS. Intrathecal injection also delivers the molecule into the CSF, but carries with it the disadvantages of possible infection, hemorrhage, and CSF leak through a tear in the dura.

For the purposes of this patent "perispinal" is to be considered as referring to "perispinal extrathecal"; therefore direct intrathecal administration is excluded from the methods discussed. Perispinal includes, but is not limited to, interspinous, interlaminar, epidural, and epidural transforaminal administration. Administration may be by injection or may involve the use of an indwelling catheter that reaches the perispinal space (epidural, interspinous, etc.). Additionally, perispinal administration may involve the use of an implanted pump or reservoir, or the use of a depot formulation, including, but not limited to a polymer depot formulation used to release a biologic TNF antagonist.

The term "treatment" as used herein in the context of treating a condition refers to treatment and therapy, whether a human or an animal, in which some desired therapeutic effect is achieved, for example the inhibition of the progression of the condition or illness, and includes the reduction in the rate of progress, a halt in the progression of an illness, amelioration of the adverse condition, and cure of the condition. Treatment as a prophylactic measure, as well as combination treatments and therapies are also included. As used herein, "therapeutically effective" refers to the material or amount of material which is effective to prevent, alleviate, or ameliorate one or more symptoms or signs of a disease or medical condition, produce clinical improvement, delay clinical deterioration, and/or prolong survival of the subject being treated. As used herein, "subject" refers to animals, including mammals, such as human beings, domesticated animals, and animals of commercial value. As used herein, "perispinal administration without direct intrathecal injection" refers to an administration method that utilizes a needle or catheter to deliver the therapeutic molecule within 10 cm of the spine, performed so that the needle or catheter does not penetrate the dura mater that surrounds the spinal cord. As used herein, "chronic brain injury of long standing" refers to a subject who has suffered a brain injury at least 12 months previously yet continues to present symptoms of brain injury. Preferred methods of the present invention also include, but are not limited to, a brain injury suffered at least 24 months, 30 months, 36 months, or 48 months previously. As used herein, "an initial dose containing a therapeutically effective amount" of therapeutic means that the subject was not treated with that therapeutic before. For the purposes of this patent, "spasticity of long standing" is defined as spasticity present for at least 24 months.

Clinical Results

Case 1

A 61 y.o. man presented to the clinic three years after a major left middle cerebral artery (MCA) stroke. 36 months earlier, following sudden onset of profound aphasia, confusion, and motor weakness the patient was taken to a local emergency room (ER). In the ER there was right hemiplegia and complete aphasia. Computed tomographic (CT) brain scan did not show bleeding. The patient was transferred to a regional hospital for consideration of intra-arterial treatment because the three-hour cutoff for initiation of intravenous (IV) thrombolytic treatment was missed. Arteriography demonstrated occlusion of the anterior branch of the left MCA. Intra-arterial reteplase infusion resulted in partial resolution of thrombus and partial reperfusion. Repeat CT scans demonstrated acute cerebral infarction in the distribution of the left middle cerebral artery with edema in the left frontal, temporal and parietal lobes and midline shift. Maximal midline shift was 11 mm six days following the stroke. The patient required 10 days of intensive care and one month of inpatient rehabilitation. While in the intensive care unit (ICU) he could not talk and had no purposeful movement in his arms or legs. After three weeks in the hospital he began to be able to move his legs. At time of discharge home there was movement in the right leg but none in the right arm and profound expressive aphasia persisted. There was also cognitive impairment: for example, he could not comprehend how to use a television remote control. Two months after the stroke he could still not speak intelligible words. With time right leg motor abilities recovered substantially, but motor function of the right upper extremity and speech remained severely limited. The patient had a previous history of hypertension, hyperlipidemia, type 2 diabetes mellitus, coronary artery disease, and myocardial infarction. Diabetes was well controlled. Current medications included aspirin and extended-release dipyridamole, extended release niacin, escitalopram, metformin, pravastatin, glipizide, and zolpidem.

At presentation to the clinic three years after the stroke, the subject's wife reported that his speech and language abilities remained severely limited; useful function of the right hand was absent and of the right upper extremity was extremely limited; there were limitations in gait including a chronic limp and inability to run; and there were persistent cognitive limitations. Included in the cognitive limitations were the inability to tell time, whether from a wristwatch or a wall clock; to dial a telephone, even when the phone number to dial was prominently displayed next to the telephone; to enter a series of four numbers into a numeric keypad, such as for a gate entry; to type a sentence on a computer keyboard, despite multiple attempts by family members to so instruct; and the inability to select the appropriate utensil for eating (he persisted in choosing a fork for sipping soup; and when using a fork or a knife would often attempt to use it oriented incorrectly, e.g. upside down). His wife reported that despite suffering repeated burns on his hands he continued to remove hot dishes from the oven without using insulated hand protection.

On examination there was severe non-fluent expressive aphasia. Motor speech was characterized by severe oral and verbal apraxia with deficits in articulatory agility and moderately impaired suprasegmental features of speech. The patient had difficulty verbalizing more than one word at a time and difficulty with correct pronunciation of single words and multiple consonants. There was a right hemiparesis involving the face, upper extremity and leg, with right hemi-anesthesia involving the face, lips, upper extremity and leg. There was spasticity of the right upper extremity. The right hand was held in a persistent flexor position with inability to extend or use the fingers. Range of motion of the right upper extremity was limited; he could not bring his right arm behind his back and could not elevate his upper arm above his head without difficulty. Raising his right arm took concentrated mental effort. He walked with a decided limp and could not ambulate quickly. Neurocognitive testing was performed. The Mini-Mental State Exam (MMSE) score was 26/30 and the Montreal Cognitive Assessment (MOCA) score was 23/30 indicating mild cognitive impairment. An activities of daily living (ADL) inventory (Alzheimer's Disease Cooperative Study Activities of Daily Living Scale) documented functional difficulty with daily tasks with a score of 61/78. Time to walk a measured 20-meter distance down the office corridor was 19.8 seconds and 23.0 seconds returning. When asked to walk quickly the times were 16.5 seconds and 17.0 returning.

Following informed consent, perispinal etanercept 25 mg was administered in aqueous solution (time zero) followed immediately by Trendelenburg positioning. Within two minutes, while still inclined on the treatment table, his speech was more distinct. Upon resuming the sitting position at five minutes he used his right arm to help reposition his body when arising from the Trendelenburg position, something that he had not been able to do in the three years since his stroke, and he stated "I woke up". At nine minutes he recited the alphabet with improved clarity of speech: the letters were more distinct and recited more quickly. At ten minutes he noted sensation in his right arm and improved mobility in his right arm. At 16 minutes he indicated that he had sensation in his right cheek; at 20 minutes sensation was present in his right ear and he was able to place a cotton swab into his right ear canal with his left hand. At 20 minutes sensation was present in his right oral cavity and in his right upper lip. At 25 minutes there was sensation in the right leg. At 27 minutes he was able to squat without difficulty. At 28 minutes he was able to walk down the hallway corridor noticeably faster than he had been able to walk before perispinal etanercept. Within 30 minutes there was reduction in right arm spasticity. At 45 minutes he was able to correctly dial a telephone number for the first time since his stroke. He spoke with his daughter, and then dialed his son's telephone number and spoke with him. Several minutes later he demonstrated that he was able to sit and arise from a deep sofa without difficulty and without assistance. He danced with his wife and demonstrated a golf swing. His standing balance was improved. At one hour a lunch break was taken. During the break his wife observed the following, all notable improvements when compared with his pre-treatment function: He chose and used a spoon correctly for sipping soup. He placed a soda glass correctly on the table in relation to the dishes in a single attempt. The liquid in the glass was not spilled when moved. Soda was obtained from the self-service dispenser without difficulty. The lunch menu was read correctly without difficulty with correct recitation of "sandwich" and "quesadilla". He ordered his own lunch from the server and his wife did not have to help with translation. He was able to read a clock in the cafeteria and recite the correct time for the first time since his stroke. He returned to the clinic. At two hours he was able to walk 20 meters in 10.1 seconds and return in 11.6 seconds. He and his wife returned to their hotel. At 46 hours they returned to the clinic. His wife reported that in the hotel two hours before (at 44 hours), for the first time since the stroke, he was able to recognize the letters on a computer keyboard and slowly type a sentence. His improvements in motor function, sensation, cognition, and behavior had all continued without diminution. Motor function had further improved: he had better physical endurance, was able to match his wife's normal walking pace and was able to run for the first time since his stroke. Sensation had further improved, returning in the right leg, ankle, and back of heel and to his right frontal scalp. Speech was less effortful, with improved clarity. He was able to count to 50 rapidly and without difficulty. He was able to consistently tell time by looking at a clock or a watch, and his wife observed that he was more conscious of time.

The patient and his wife returned home. At home he was able to shave his entire face with a manual razor for the first time since the stroke, and did so every day. His wife attributed this to a combination of his renewed ability to feel the right side of his face, improved spatial control of his left hand, and improved dexterity of his left hand. His wife noted that he had begun speaking with others during their everyday life, and that family members noted that his speech was more distinct and more easily understood. He remembered to use an insulated hot pad when removing dishes from the oven.

He returned to the clinic 22 days later. All clinical improvements had been maintained. A repeat ADL inventory score improved to 65/78. Repeat neurocognitive testing was performed. MMSE improved to 28/30, and MOCA improved to 27/30. The patient requested another dose of etanercept. After obtaining written consent, 25 mg perispinal etanercept in aqueous solution was administered followed by five minutes of Trendelenburg positioning as before. Within ten minutes of this second etanercept dose his speech appeared to be more distinct with improved articulation of sounds. Eight hours later he was able to dorsiflex his right wrist for the first time since the stroke. The following day in the clinic volitional right wrist dorsiflexion and visible activation of the right hand second dorsal interosseous muscle were observed. Speech was more distinct.

One month after the first dose there was further improvement in strength of his right arm and in clarity of speech. He was able to remove the twist-off tops of bottles for the first time since the stroke. At five weeks he was able to correctly drive a manual transmission automobile. He had previously attempted this prior to etanercept administration but was unsuccessful, as he was unable to co-ordinate the clutch/ accelerator and shift activities. At seven weeks, clinical improvement was maintained and no adverse effects had been experienced. Clinical improvement has persisted for more than 10 months.

Case 2

Figure 2:
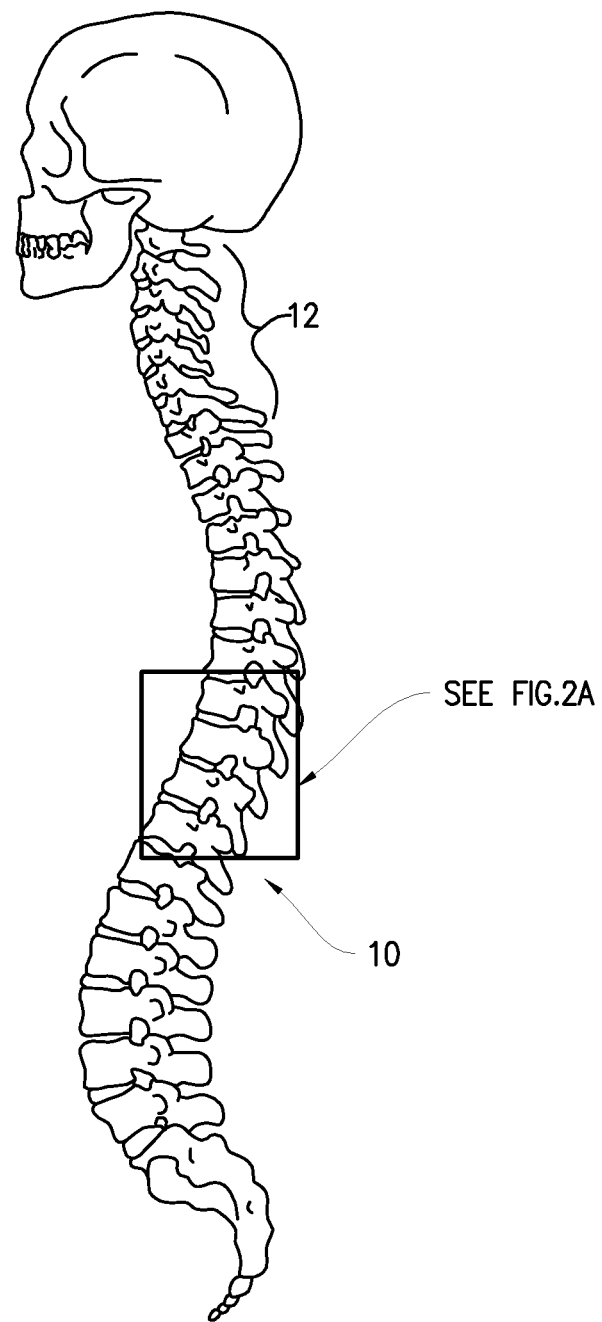
FIG. 2 is a drawing depicting a view from the side of a cross-section of the skull and the spine of a human.
Figure 2A:
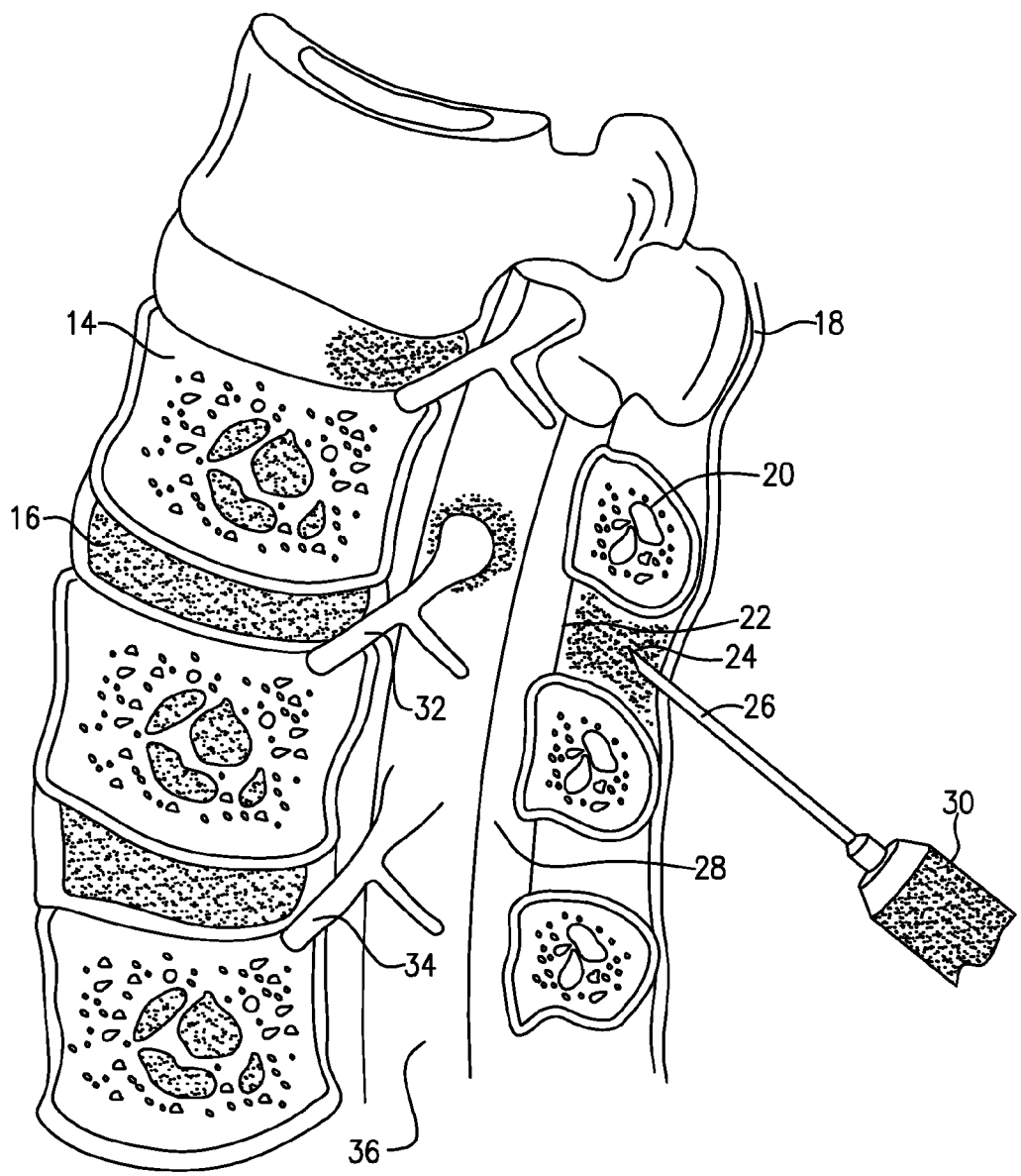
FIG. 2A is a diagram depicting perispinal administration to a humanA, in accordance with the present invention.

A 49 y.o. man presented to the clinic 35 months after a brainstem stroke. Three years earlier he had awoken with paresthesia in the left arm and leg, followed by increasing weakness of the left arm and leg. In the ER his symptoms worsened. MRI of the brain revealed a right medullary infarction (FIG. 2). The patient required eight days of acute hospitalization and one month of inpatient rehabilitation. Left leg motor recovery began after one to two weeks but the patient was left with a severe residual gait disturbance and severe paresis of the left upper extremity. Initially there was also transient left facial paresthesia and speech difficulty, both of which resolved within two weeks. At time of discharge home walking was only possible with the assistance of a walker or a quad cane, and there was hypoesthesia in the left upper and lower extremities, with painful paresthesia in the left upper extremity. At presentation to the clinic all of these neurological deficits had been stable for at least one year without change. The patient had a history of hypertension and type 2 diabetes mellitus. Diabetes was well controlled. Current medications included amlodipine, metformin, metoprolol, losartan, simvastatin, clonidine, gabapentin, glipizide, aspirin and extended-release dipyridamole and liraglutide.

On examination he had difficulty maintaining his balance upon standing without using his right arm for assistance. He had a left hemiparesis, with severe weakness of his left upper extremity, moderate weakness of the left lower extremity, and hypoesthesia of his left extremities. Speech and cognition appeared normal. Walking was slow, requiring 1:56 minutes going and 2:03 minutes returning to walk the 20 m office corridor distance using a standard walker for assistance.

Following informed consent perispinal etanercept 25 mg was administered in aqueous solution, followed immediately by five minutes of Trendelenburg positioning. At 9 minutes following the etanercept dose the patient stood up from the exam table. His standing balance was notably improved and was accomplished without difficulty and without use of the right arm for stabilization.

At 30 minutes he again walked the 20 m office corridor distance with a standard walker for assistance. Times to complete were 1:20 minutes going, 1:21 returning. Walking required visibly less effort. The patient returned at 10 days. He walked the 20 m office corridor using a standard walker for assistance. Times to complete were 1:06 minutes going, 1:11 returning. At 17 days the patient returned to the clinic. He reported maintenance of his clinical improvement, with walking continuing to be faster and to require less effort than prior to etanercept. He also said that he felt that he was able to incorporate his left arm in normal daily activities (to the extent possible) with less effort. On examination his stride was longer and his gait more fluid than prior to perispinal etanercept administration. Improved walking speed was maintained, with time to walk 20 m with a standard walker measured at 1:13 down the corridor and 1:10 back. At the end of three weeks the clinical improvements were maintained. At 24 days, after written informed consent, a second 25 mg dose of perispinal etanercept was administered. At 10 minutes after the dose, time to walk 20 m with a standard walker was measured at 1:03 down the corridor and 1:03 back. At one month after the first dose clinical improvement was maintained, including improvement in walking ability and subtle improvements in motor control of his left upper extremity. No adverse effects of etanercept were noted.

Case 3

A 58 y.o. man presented to the clinic 13 months after a right MCA territory stroke. On the day of the stroke left-sided weakness began in the morning abruptly. In the ER he had a left hemiparesis, no spontaneous movement in the left upper extremity, 2/5 movement of the left lower extremity, a left facial droop, and was unable to move his eyes to the left. Brain CT initially showed no bleed and CT angiogram showed a 1 to 1.5 cm clot in the right MCA. Subsequent brain CT showed acute infarction in the territory of the right MCA. Acute thrombolytic therapy utilizing intravenous recombinant tissue plasminogen activator was given followed by increasing mental confusion but improved vision and control of the left lower extremity. He was transferred into the ICU. Repeat CT showed a 0.75 square centimeter bleed in the pons in addition to the right hemispheric stroke, with a subsequent CT at six days showing a stroke in the distribution of the right MCA with a mass effect from cerebral edema compressing the right lateral ventricle (FIG. 3). He was managed in the ICU for seven days and then transferred to inpatient rehabilitation. After 10 days he was able to walk with some assistance. He was discharged home after five weeks. At the time of discharge home he had a persistent left hemiparesis, with left facial droop, clumsiness of his left upper extremity and severe functional difficulty using his left hand, mild weakness of the left leg, hypoesthesia of the left upper extremity, left leg and foot, and constant pain in his left arm and hand that was exacerbated by firm gripping with the left hand. The patient had a history of hypertension, hypercholesterolemia, and coronary artery disease.

Upon presentation to the clinic the patient reported no improvement in his neurological symptoms for at least the past six months, with persistence of all listed neurologic deficits. He reported severe difficulties using his left hand: inability to perform fine movements, such as stuffing envelopes; difficulty dressing, with inability to buckle his belt or unbutton buttons, and difficulty preparing food, with a tendency to burn his hand. He reported difficulty in placing postage stamps on an envelope in the correct orientation. He noted that he could not correctly gauge the spatial location of his hand with his eyes closed: he could not tell if it was up, down, in front, or in back of his body. Since his stroke he had been unable to place his hand in his pants pockets, either front or back due to both his inability to direct his hand in space accurately and also the fact that his first remained clenched. He was able to hold objects in his left hand but could not maintain the grip without constant attention: when he held liquid in a cup he would spill or drop it. He could not control the pressure of the grip of his left hand. His current medications were lisinopril, simvastatin, aspirin, gabapentin, and venlafaxine.

On examination there was a left facial droop, increased tone and spasticity in the left upper extremity, a mild left hemiparesis, and resting closed flexion of the left hand. The left hand was clumsy, with dysdiadochokinesis. Left hand tapping rate was slow (measured at 2.8 Hz). There was marked difficulty with two-handed handling and folding of letter paper. There was left hemi-hypoesthesia with inability to sense pinprick. Seated with his eyes closed with both arms held out the left arm drifted upward. There was dysdiadochokinesis of the left hand. Hand grip strength was left/right=32/36. The left hand grip strength test produced marked discomfort in the left hand. There was balance difficulty while standing with the eyes closed. The patient walked with a persistent clenched first and with a slight limp. Times for walking 20 m in the office corridor were 13 seconds out and 14 seconds back. On neurocognitive testing, MMSE was 26/30 and MOCA was 23/30, indicating borderline impairment.

Following informed consent perispinal etanercept 25 mg was administered in aqueous solution (time zero) followed immediately by five minutes of Trendelenburg positioning. Following etanercept the following improvements were noted: beginning at seven minutes his left facial droop had improved; at eight to ten minutes his left hand exhibited improved dexterity, tapping speed was faster (left hand tapping speed was videotaped and measured at 5.5 Hz), left hand diadochokinesis was faster and left hand finger-to-nose was faster; at 11 to 15 minutes sensation in the left cheek, hand, arm, and shin were improved; there was increased strength in the left knee extensors and the hands, with hand grip strength left/right=36/40, and he was able to correctly perceive the spatial location of his left hand. Firm gripping during the left hand grip strength test did not produce pain. At 16 minutes he was able to place his left hand in both his left front and left back pants pockets for the first time since his stroke and his gait was more fluid. At 20 minutes he was able to buckle his belt with his left hand. Within 45 minutes he was able to open a water bottle, hold a water bottle without dropping it and page through a magazine, all with his left hand, all tasks he could not similarly accomplish prior to etanercept, and the pathological upward drift of his left arm with his eyes closed present prior to etanercept administration was markedly reduced.

At 48 hours he reported maintenance of all clinical improvements. He was no longer spilling his coffee cup when held in his left hand and had less pain in this left arm and hand. He reported that his sense of balance while walking was improved. At seven days all previous clinical improvements were maintained. In addition he reported improvement in memory and conversational abilities, was able to buckle and unbuckle his belt and button and unbutton buttons and reported improved ability to use his left hand in everyday tasks. Hand grip strength was left/right: 40/40. At 13 days his previous clinical improvements were maintained, and there was evidence of additional improvement. His gait was more fluid and he noted his balance while walking was better. Times for walking 20 m were 10 seconds out and 10 seconds back. During conversation there was notably more expressive movement with the left arm and hand. The patient's partner said that at home his improved abilities to use his left arm and hand were remarkable, and that one week after the dose of etanercept he was able to pick up single playing cards and deal cards with his left hand, tasks he had been unable to perform with that hand prior to receiving etanercept. On repeat neurocognitive testing MMSE was stable at 26/30, MOCA was significantly improved at 29/30, and on examination he was able to deal playing cards with his left hand and pick up single playing cards with his left hand as his partner had reported. At 20 days the patient reported that the clinical improvement in his left hand had begun to diminish. At 26 days he returned to the clinic. He was able to manipulate shoe laces with his left hand with some difficulty, a task he was unable to perform prior to etanercept, but he reported that motor control of his left hand was not as good as it had been ten days earlier. After written informed consent a repeat 25 mg dose of perispinal etanercept was administered. Following the dose within thirty minutes he was able to lace his own shoes using his left and right hands together more easily than prior to the dose and improvement in his left facial droop was noted. At one month clinical improvement from baseline continued with no adverse effects noted.

Case 4:

A 37-year-old right-handed male who had sustained a severe traumatic brain injury with residual deficits 20 years previously, at the age of 17, when he was involved in an automobile accident. At the time he was hospitalized and comatose for three months, and after regaining consciousness required further hospitalization for rehabilitation for an additional six months. He suffered a right hemiparesis, severe memory impairments and motor and co-ordination difficulties bilaterally. He was able to finish high school two years later in a wheelchair. Prior to treatment he complained of difficultly with motor control, with loss of dexterity more prominent on the right than on the left side, and having difficultly completing simple tasks because of motor deficits as well as being dependent on a wheelchair.

Neurological examination revealed speech that was articulated with normal amplitude in a hypo-productive, indistinct, slowed and slurred quality with mild dysarthria. He was tested with a standarized, normed test of letter verbal fluency, the FAS test. He listed nine words starting with the letter F, four words starting with the letter A and eight words starting with the letter S in a 60 second trial period for each letter. It took the patient 16 seconds to read a list of ten words of increasing complexity. His affect was labile, fluctuating from a euthymic relaxed jocular state to becoming easily angered and irritable. He had mildly impaired simple attention performing serial three subtraction, subtracting down from 100 to 29 in 105 seconds but then stopping making one error. It took over 10 seconds to attempt to spell the word "world" backwards making one error. He could not perform serial sevens. He was able to list the days of the week in reverse order but took 10 seconds to perform this task, below expectation. He was not able to list the months of the year in reverse order. Abstractions: the patient was able to tell me how a watch and ruler, or train and bicycle were similar, but could not tell me how honesty and charity were similar. Memory: The patient took three repetitions to retain three memoranda but after five minutes the patient could not retrieve any of the memoranda. He could not remember his examiner's name despite four repetitions throughout the examination. Cranial nerves: pupils were 3 mm and one plus reactive directly and consensually to light. His visual fields were full to confrontation and extra ocular motions were conjugate and full. Bell's phenomena deviated to the right. There was full facial sensation but facial asymmetry was noted with a wider palpebral fissure and flattening of the nasolabial fold appreciated on the left side. He had normal palate, normal sternocleidomastoid, normal trapezius and normal tongue functioning. Motor: He maintained his right upper extremity in somewhat of a flexed abducted posture with intermittent ataxic and dystonic axial motion i.e., slow-moving in a seated position. He had loss of fine motor control of his right hand with slowed finger to finger and incomplete grasp of the right upper extremity. He had marked clasp knife tone of his right upper extremity and a right sided pronater drift and Hoffman sign more prominent on the right but also present on the left. There was an extensor toe response more prominent on the right but also present on the left. There was marked slowing of rapid alternating movement in the right upper extremity, moderate slowing of the left with mirror movement. He had full strength of his proximal upper extremities, both lower extremities and his left hand. He had impaired heel to knee and heel to shin more prominent on the right but also on the left. There was equinus posturing of his right lower extremity with a subtalar Charcot joint. He was able to walk with impaired balance using a walker taking 174 seconds to walk 20 meters. Joint position, pinprick, vibration and light touch was intact.

Following written informed consent, 25 mg aqueous etanercept was administered by perispinal injection without direct intrathecal injection. More specifically, etanercept was administered by perispinal injection overlying the posterior cervical spine within five centimeters of the spinal cord but external to the ligamentum flavum, in the interspinous space. The injection was extrathecal. The injection was followed by brief prone positioning for 30 seconds and then the examination table was tilted with the head below horizontal, in the Trendelenburg position. Repeat neurological examination was performed 15 minutes after perispinal etanercept administration.

Results: The patient appeared more relaxed with less analgic shifting. His speech pattern was markedly improved with a decrease in the dysarthric indistinct quality and an increase in the speed of production that was apparent to all observers. His ability to read a simple story and abstract concepts was compared in a pre- and post-administration form where the speed of reading increased from 89 seconds before perispinal etanercept to 64 seconds after perispinal etanercept administration. He was unable to initially abstract the concept of a short story prior to perispinal etanercept but after use perispinal etanercept was able to abstract the concept. His ability to read a list of increasing complex words was objectively improved, in both clarity and the time to completion of task was decreased, taking ten seconds to read the identical word list, a significant improvement. Following perispinal etanercept his FAS score improved by a total of eight words, (−1) words beginning with F, (+8) words beginning with A, and (+3) words beginning with S. He used six identical words in the pre- and post-test scores.

His ability to move appeared more fluid with a noticeable and significant decrease of his ataxic spasticity. The clasp knife tone of his right upper extremity was improved as well as his ability to perform rapid alternating movements. His gait although still impaired and slowed appeared more fluid and less patterned. His posture appeared less ataxic and less analgic. His time to walk 20 meters was significantly faster, 134 seconds.

Laboratory data: A three Tesla MRI examination of the brain was performed which revealed bilateral lateral ventricular dilatation more marked posteriorly with cortical atrophy, a dilated right anterior temporal horn and atrophy of the head of the hippocampus. There was atrophy of the entire corpus callosum. Hemosiderin deposition was noted in the left posterior paraventricular white matter extending to the left posterior centrum semiovale with a discrete small focus in the left putamen and right posterior limb of the internal capsule. Diffusion tensor imaging showed white matter track loss bifrontally and biparietally, more prominent on the left than the right.

The patient was examined weekly for one month following the single initial perispinal etanercept dose. He remained significantly clinically improved for the entire one month period, with improved balance, clarity of speech, decreased spasticity, more fluid gait, improved attention, and improved mood. He reported that it was easier for him to perform motor tasks including walking and dressing.

Case 5:

A 23 y.o. man sustained a mild traumatic brain injury two years previously due to immediate proximity to an explosion while in military combat. Two years earlier in Iraq he was hit by a blast from an IED (improvised explosive device). The explosion knocked him down. He could not move or talk for a brief period of time. At the time his MACE (Military Acute Concussion Evaluation) score was 21/30. Two years after the explosion he exhibited trouble calculating, spelling, reading; difficulty sleeping; headaches; light sensitivity, easy arousal and startle responses, and change in personality (more anger, irritability and frustration). He demonstrated irritability and outbursts of anger at work and at home. He reported nightmares, avoidance of situations that would remind him of his blast injury, being constantly on guard, watchful, and easily startled. Following the explosion he developed bilateral upper extremity dysmetria resulting in bilateral intention tremor, difficulty arising from a sitting position, impairment in immediate memory and cognition, and adverse changes in mood and affect all of which persisted and were found to be present upon his presentation to the clinic.

Examination revealed reduced attention, concentration, reading abilities, and abnormal scores on standarized cognitive testing. He seemed irritable and somewhat withdrawn. Mini-mental state examination score was 22/30; Montreal Cognitive Assessment score was 20/30. MACE score before treatment was 24/30. The patient fulfilled the DSM-IV-TR criteria for PTSD.

Magnetic resonance imaging of the brain was read as normal. After neurologic examination written informed consent for the perispinal administration of etanercept was obtained. Etanercept in sterile water as administered by perispinal injection in the interspinous space superficial to the ligamentum flavum between the sixth and seventh cervical spinous processes while the patient was sitting on the examination table. The injection was extrathecal. The patient was then placed supine on the table, and then turned into the prone position. While he was turning he reported the onset of a euphoric-like sensation (which persisted for approximately 18 hours). He was then placed in the Trendelenburg position for five minutes, with the examination table tilted with the head below horizontal, and then returned to the sitting position.

Results: The patient had onset of clinical improvement within two minutes of perispinal etanercept injection, even before assuming the Trendelenburg position. At ten minutes following injection there were significant and noticeable improvements in posture, range of motion, ability to arise from the sitting position, improvement in bilateral intention tremor, and improvement in immediate memory and cognition. His mood was improved, and his personality had changed. He was more affable and the irritability was gone. MMSE improved by two points to 24/30; there was improvement in reading and number span. At two weeks after a single 25 mg perispinal dose of etanercept there were continued and marked improvements in multiple PTSD symptoms, including those associated with intrusive recollection and hyperarousal. Interactions with co-workers improved. The improvements were clinically significant and prolonged. There were improvements in PTSD symptoms and signs, including improvements in mood, cognition, and behavior as a result of etanercept administration. The patient was followed as an outpatient. He had persistent clinical improvement in motor function, cognitive abilities, irritability, mood, and work performance.

Case 6:

A 46 y.o. man had suffered a head injury secondary to a car accident in 1988 that left him comatose for six weeks. The accident has left him with persistent left hemiplegia, dysarthria, visual disturbances (diplopia and nystagmus), cognitive weaknesses, and difficulties with memory and attention.

Six days prior to the patient's visit to the clinic neuropsychological testing was performed documenting a lowered neurocognitive profile suggestive of diffuse cerebral dysfunction. Category verbal fluency (animal naming) was borderline to low average, with a score of 15 (8-10 percentile) (normal mean=21.9 SD=5.4). Visual recognition of the slope of lines (Judgement of Line Orientation (JLO)) was low average with a score of 22/30 (22 percentile). Six days following neurocognitive testing the patient presented for examination. This clinic visit was 22 years after the automobile accident that had caused severe traumatic brain injury. He came to the clinic in a wheelchair with an obvious left hemiplegia, slurred speech, diplopia, nystagmus, and inability to walk without assistance.

Motor skills of his left extremities were examined. Movement of his left extremities required extreme mental effort. There was increased tone (spasticity) of left arm, hand, fingers, and left leg. Movement of the fingers was severely impaired. Movement of the left wrist was impaired. Movement of the left upper arm was greatly impaired. Movement of the left heel down the left shin appeared to require extreme mental effort and was impaired. The patient was unable to ambulate with a quad cane without substantial physical assistance. Ambulation required extreme mental and physical effort. The patient was unable to transfer into or out of his wheelchair without substantial physical aid.

Reading skills were carefully examined. The patient was given multiple short stories to read aloud prior to etanercept administration. The patient exhibited dysarthria, slurred and indistinct speech, and impairments in reading comprehension, cadence, content (skipped words and phrases) and intonation. Reading speed was substantially impaired. While speaking there was asymmetry of the face.

Following written informed consent, aqueous etanercept 25 mg was administered by perispinal injection without direct intrathecal injection. More specifically, etanercept was administered by perispinal injection overlying the posterior cervical spine within five centimeters of the spinal cord but external to the ligamentum flavum. The injection was extrathecal. The injection was followed by brief prone positioning for 30 seconds and then the examination table was tilted with the head below horizontal, in the Trendelenburg position.

There was clinical improvement noted within two minutes of injection, with his speech being clearer. After resuming the sitting position there was improvement in the patient's facial symmetry. The patient was able to transfer to his wheelchair with much less difficulty. Finger movements on the left hand were improved. Spasticity of the left upper extremity was decreased. There were multiple improvements in motor function. One to two hours after etanercept administration the patient was re-examined. There were noticeable and significant improvements in distinctness of speech, motor abilities of the left extremities, including increased range of motion of the left arm, wrist, hand, and fingers; decreased spasticity of both left extremities, and the patient was able to walk with a single quad cane with minimal assistance, for the first time in twenty two years. Reading abilities were re-tested. There was improved reading comprehension; speech was less slurred and more distinct; cadence and intonation and phrasing were improved; and reading speed was improved more than 30%. Mood, affect and irritability were improved. On the day following perispinal etanercept administration repeat neurocognitive testing was performed. Category verbal fluency (animal naming) was improved, with a score of 19 (27-29 percentile), within the normal range. Visual recognition of the slope of lines (Judgement of Line Orientation (JLO)) was improved, with a score of 28/30 (72 percentile), within the normal range. The patient was followed as an outpatient. He had persistent clinical improvement in motor function, cognitive abilities, affect, and mood.

Case 7:

An 85 y.o. man developed acute onset of nausea, vomiting, headache, vertigo, and inability to walk without falling over. He had polycythemia vera, atrial fibrillation, and a history of a recent vertebrobasilar transient ischemic attack and a myocardial infarction twenty years earlier. His medications included propranolol, aspirin, warfarin, and hydroxyurea. He was taken to the emergency room where a CAT, MRI and MRI scans revealed a posterior cerebellar stroke on the left with a congenital absence of the left posterior inferior cerebellar artery. The patient had persistent severe vertigo, nystagmus, and inability to ambulate without assistance. Three days following the stroke, following written informed consent, etanercept 25 mg was administered by perispinal injection without direct intrathecal injection. More specifically, etanercept 25 mg was administered by perispinal injection overlying the posterior cervical spine within five centimeters of the spinal cord but external to the ligamentum flavum. The injection was extrathecal. The injection was followed by brief prone positioning for 30 seconds and then the head was tilted down below horizontal with the upper body inclined downward for five minutes.

The patient resumed the supine position. Within five minutes the patient was clinically improved. His vertigo largely resolved, his nystagmus was less marked, and he was able to ambulate without assistance. He was discharged home the next day. The patient had lasting clinical improvement, although he had balance difficulties that lasted for several months.

Additional Clinical Experience

Three of the clinical cases described above have been published by the inventor (Tobinick E., *CNS Drugs*. 2011 February; 25(2):145-155). There is now clinical experience utilizing perispinal etanercept for more than 250 individuals who had persistent neurological dysfunction following brain injury due to stroke, cerebral hemorrhage, subarachnoid hemorrhage, anoxia, cardiac arrest and other forms of brain injury. The majority of patients treated have exhibited rapid improvement in neurological function. Rapid and sustained reduction in spasticity, beginning within minutes of the first dose of perispinal etanercept is characteristic. Improvements in cognition, attention, speech, dysarthria, aphasia, motor function, sensation, hearing, taste, swallowing, vision, gait, depression, anxiety and behavior have been observed in multiple patients. The patients have been treated typically months or years following their stroke or other form of brain injury, with persistent stable neurological deficits for months or years prior to perispinal etanercept administration. They therefore typically have had a stable chronic baseline of neurological disability and dysfunction that facilitated detection of a treatment effect. Most often these patients had strokes that were 2 to 10 years earlier, but clinical improvement has been noted in patients with strokes as much as 35 years earlier.

Discussion of the clinical results: A single dose of perispinal etanercept led to immediate and sustained clinical improvement in patients with brain injury, including stroke and traumatic brain injury. Prior to these clinical results the scientific community would consider it implausible that these results could be possible; that they could occur so rapidly; or that they could be sustained from a single dose.

The most surprising aspect of these clinical results, however, is the fact that they occurred at a time so remote from the injury. The scientific community, and a person of ordinary skill in the art, would not have expected that patients who had brain injury months earlier would respond to anti-cytokine treatment; and they certainly would not have expected that patients who had brain injury years earlier would respond to anti-cytokine treatment. There is no precedent for this type of result and no clinical or basic science data of which one of ordinary skill in the art would be aware to suggest that there should be clinical response two years or more after a brain injury. The clinical results documented are scientifically unprecedented and surprising. Nevertheless they have been reproducible and consistent following perispinal etanercept administration.

FIG. 1 depicts the anastomoses between the cranial and vertebral venous systems. Perispinal administration for delivery to the brain and other structures of the head is preferably performed by a percutaneous injection into an interspinous space in the posterior cervical area (12 in FIG. 2). As shown in more detail in FIG. 2A, hollow needle (26) containing etanercept (or other therapeutic molecule of this invention) in solution (30) is injected through the skin 18 into the interspinous space 24. If the needle were carried further it could penetrate the ligamentum flavum (22), delivering the therapeutic molecule into the epidural space (28) surrounding the spinal cord (36), although in this invention in several preferred embodiments the ligamentum flavum is not penetrated by the needle, and the therapeutic molecule is deposited into the interspinous space more superficially, without penetration of the ligamentum flavum. The therapeutic molecule in the interspinous space drains into the vertebral venous system, and is then carried to the brain and other structures of the head; (34) is a spinal nerve root.

Figure 3A:
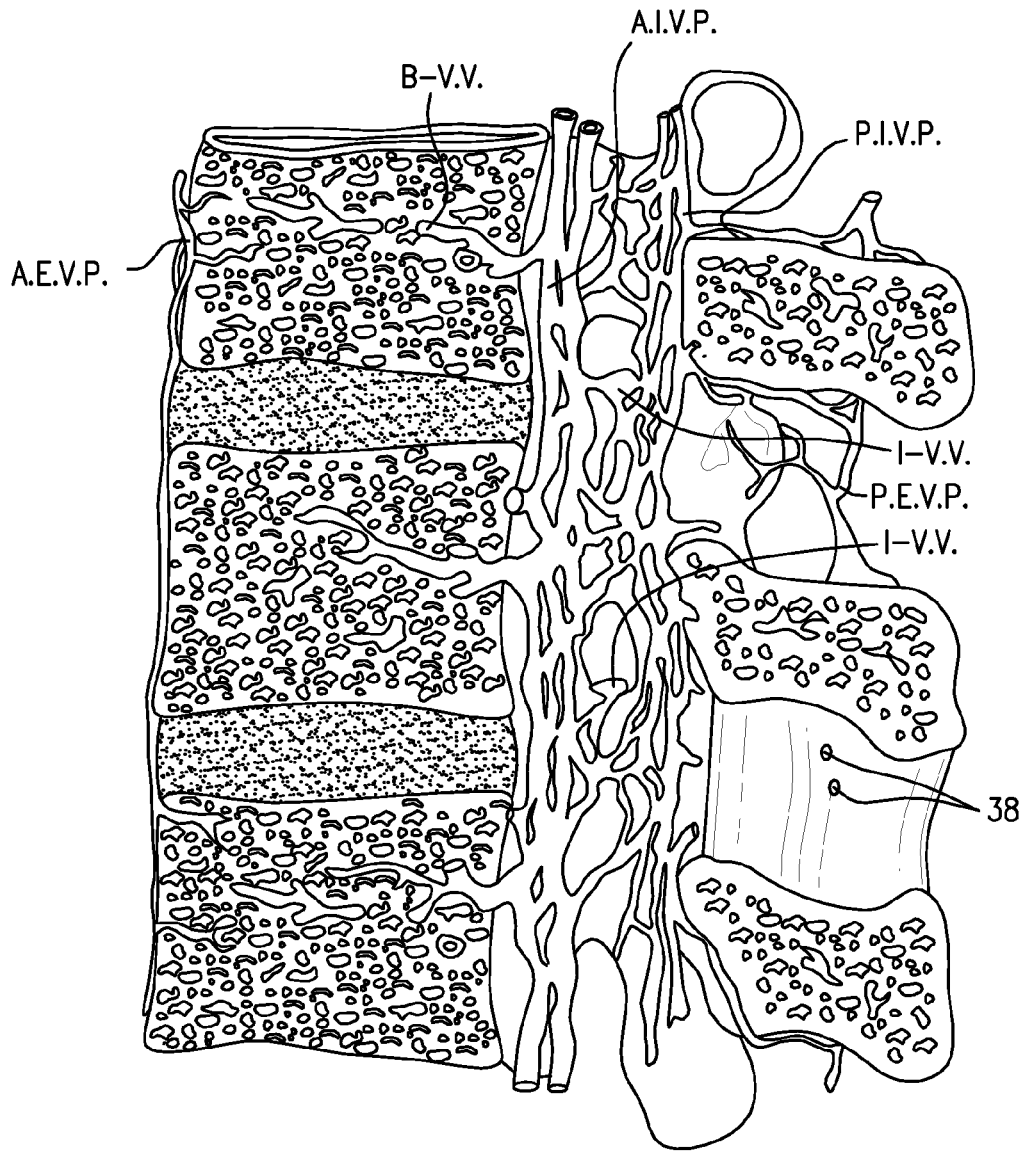
FIG. 3A is an enlarged elevational cross sectional view of the spinal area and the vertebral venous system (VVS) and its anatomic relationship to the interspinous space and other anatomic elements of the spine.
Figure 3B:
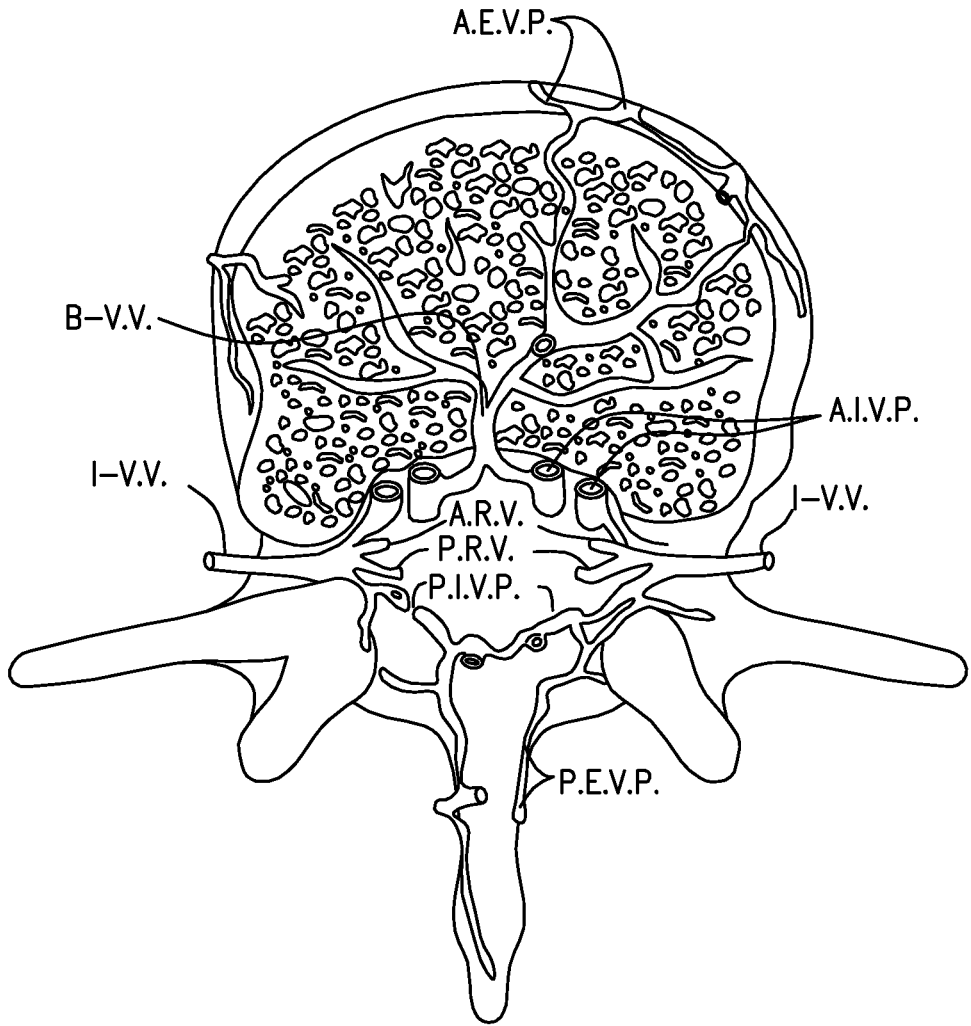
FIG. 3B is an enlarged horizontal cross sectional view of the spinal area and the vertebral venous system and its anatomic relationship to the interspinous space and other anatomic elements of the spine.
Figure 3C:
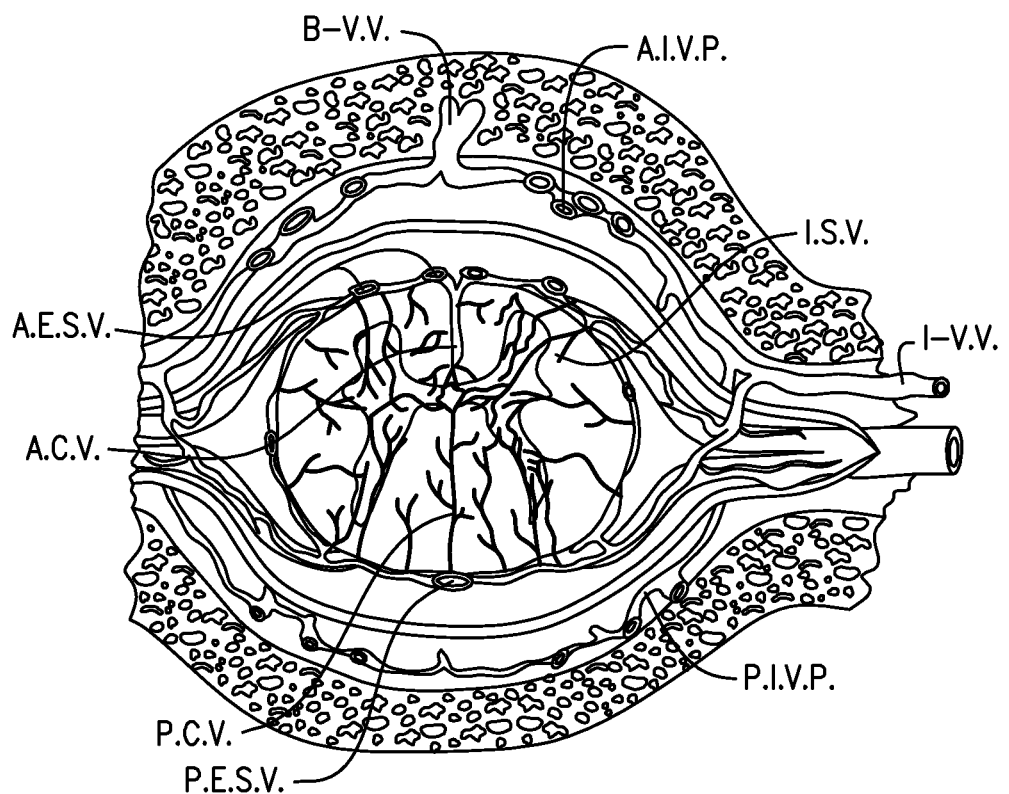
FIG. 3C is an enlarged horizontal cross sectional view of the spinal area and the VVS and its anatomic relationship to the interspinous space and other anatomic elements of the spine.

The interspinous space (24) is defined as the space between two adjacent spinous processes (20). FIG. 3A shows the interspinous space (24) having veins (38) (FIG. 3A) which collect the therapeutic molecule, e.g. etanercept, which reaches the interspinous space after percutaneous interspinous injection and which veins drain the therapeutic molecule into the VVS, so that using the physical maneuvers of the present invention, the therapeutic molecule is transported via retrograde venous flow into the intracranial veins via the anastomoses shown in FIG. 1, and then to the brain or other structures of the head.

The vertebral venous system is used in a non-obvious way for the present inventions because a venous system is routinely conceptualized as a system that drains blood from a target area or organ. For example the venous system which drains the kidneys is widely acknowledged to be a vascular system that drains blood from the kidneys, not as a way of delivering a therapeutic molecule to the kidneys. Likewise the venous system of the brain is widely medically recognized as a system which functions to drain blood from the brain. It would be counter-intuitive to propose using the CSVS to deliver a therapeutic molecule to the brain, by conventional thinking. Likewise the use of the CSVS to achieve delivery of therapeutic compounds to the brain is not obvious, because conventional thinking is that this venous system functions to drain venous blood away from these anatomic sites. Therefore the inventions of consideration here are in this way counter-intuitive, because they rely on the vertebral venous system to deliver therapeutic molecules (including specifically large molecules) to the brain, cerebrospinal fluid, or the head. This delivery is accomplished by retrograde venous flow (opposite from the usual direction), that is facilitated by the proper use of gravity and positioning of the patient so that venous flow in the desired direction is accomplished. The rich connections between the cranial venous system and the vertebral venous system were beautifully depicted by Breschet (Breschet G. *Recherches anatomiques physiologiques et pathologiques sur le systáeme veineux* (Rouen fráeres, Paris, 1829), but this anatomic route still remains largely unrecognized by the medical community.

Dosages and Routes of Administration

The therapeutically effective dosage of a biologic used for perispinal administration superficial to the ligamentum flavum (such as interspinous injection) will in general be 10% to 100% of the dosage used as a single dose for systemic administration. The therapeutically effective dosage of a biologic used for epidural administration will in general be 2% to 100% of the dosage used as a single dose for systemic administration The dosage used for systemic administration is well known by those skilled in the art as it is specified in the FDA approved literature which accompanies each of these biologics. For example, if the usual dose when administered systemically is 50 mg, then the dose used for interspinous administration will usually be between 5 mg and 50 mg.

Etanercept may be administered to the perispinal area by interspinous injection at a dose of 5 mg to 100 mg given from once per week to once per 3 months. It will be appreciated by one of skill in the art that appropriate dosages of the compounds, and compositions comprising the compounds, can vary from patient to patient. The determination of the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Definitions provided herein are not intended to be limiting from the meaning commonly understood by one of skill in the art unless indicated otherwise. The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

An advantage of the present invention is that it identifies and selects the use of biologics as effective therapeutic agents for treatment of BI. More specifically an advantage of the present invention is that it identifies and selects the use of TNF antagonists as effective therapeutic agents for the treatment of a mammal after BI, even long after the initial BI event, such as long after completion of a stroke. Accordingly, an advantage of the present invention is that it provides for the delivery of a biologic to the CSVS and thenceforth delivery of a therapeutically effective dose of the biologic to the brain, as a new biologic treatment of a human with BI; such that the use of the biologic will result in clinical improvement, or will slow progression of the underlying pathologic process. Accordingly, an advantage of the present invention is that it provides for the delivery of etanercept to the vertebral venous system and thenceforth to the brain of a human with BI; such that the use of etanercept will result in clinical improvement, or will slow progression of the underlying pathologic process. Another advantage of the present invention is that it provides for a biologic delivered by perispinal administration, thereby delivering the biologic into the vertebral venous system and thenceforth the brain of a human with BI, which, when compared to systemic administration, produces one or more of the following: greater efficacy; more rapid onset; longer duration of action; improved delivery to the CNS; or fewer side effects. Another advantage of the present invention is that it provides for one of a group of biologics, as specified herein, which affect neuronal or immune function, delivered by retrograde venous flow in the CSVS (through the vertebral venous system into the cranial venous system), thereby facilitating delivery of the biologic to the brain of a human following BI for therapeutic purposes.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

REFERENCES

1. Batson O V. *Annals of Surgery,* 112, 138-149 (1940).
2. Groen R J, du Toit D F, Phillips F M et al. *Spine,* 29(13), 1465-1471 (2004).
3. Groen R J, Groenewegen H J, van Alphen H A, Hoogland P V. *Anat Rec,* 249(2), 285-294 (1997).
4. Tobinick E. *Expert Review of Neurotherapeutics,* 10(6), 985-1002 (2010).
5. Tobinick E L, Chen K, Chen X. *BMC Res Notes,* 2, 28 (2009).
6. Breschet G. *Recherches anatomiques physiologiques et pathologiques sur le systáeme veineux* (Rouen fráeres, Paris, 1829).
7. Cao Q, Cai W, Li Z B et al. *Eur J Nucl Med Mol Imaging,* 34(11), 1832-1842.
8. Robinson W H, Genovese M C, Moreland L W. *Arthritis Rheum,* 44(9), 1977-1983.
9. Banks W A, Plotkin S R, Kastin A J. *Neuroimmunomodulation,* 2(3), 161-165.
10. Anderson R. *J Neurosurg,* 8(4), 411-422 (1951).
11. Batson O V. *American Journal of Roentgenology,* 78(2) (1957).
12. Byrod G, Olmarker K, Konno S, Larsson K, Takahashi K, Rydevik B. *Spine,* 20(2), 138-143 (1995).
13. Byrod G, Rydevik B, Johansson B R, Olmarker K. *J Peripher Nerv Syst,* 5(4), 218-226 (2000).
14. Clemens H J. *Die Venensysteme der menschlichen Wirbseáule; Morphologie und funktionelle Bedeutung* (De Gruyter, Berlin, 1961).
15. Eckenhoff J E. *Surg Gynecol Obstet,* 131(1), 72-78 (1970).
16. Gisolf J, van Lieshout J J, van Heusden K, Pott F, Stok W J, Karemaker J M. *J Physiol,* 560(Pt 1), 317-327 (2004).
17. Pardridge W M. *NeuroRx,* 2(1), 3-14 (2005).
18. San Millan Ruiz D, Gailloud P, Rufenacht D A, Delavelle J, Henry F, Fasel J H. *AJNR Am J Neuroradiol,* 23(9), 1500-1508 (2002).
19. Vogelsang H. *Intraosseous spinal venography* (Excerpta Medica, Amsterdam, 1970).
20. Ye J, Yang L, Del Bigio M R et al. *J Thorac Cardiovasc Surg,* 114(4), 660-665.
21. Tobinick E. CNS Drugs. 2011 February; 25(2):145-155.

The invention claimed is:

1. A method for treating spasticity associated with a chronic brain injury, comprising: administering to a perispinal area of a human who has suffered a brain injury at least 3 months previously and is experiencing spasticity, a therapeutically effective amount of etanercept for treating spasticity.

2. The method of claim 1, wherein said human suffered a brain injury at least 24 months previously.

3. The method of claim 2, wherein the brain injury was a stroke.

4. The method of claim 1, wherein said human suffered a brain injury at least 36 months previously.

5. The method of claim 4, wherein the brain injury was a stroke.

6. The method of claim 1, wherein the etanercept is administered without direct intrathecal injection.

7. The method of claim 1, wherein the etanercept is administered external to ligamentum flavum.

8. The method of claim 1, wherein said human also has a condition selected from the group consisting of a mood disorder, sleep disorder, cognitive disorder, aphasia, hemiplegia, sensory deficit, post-traumatic stress disorder and pain.

9. The method of claim 1, wherein said human is placed in a Trendelenburg position after administering etanercept.

10. The method of claim 1, wherein etanercept is administered epidurally.

11. The method of claim 1, wherein the brain injury was a stroke.

12. The method of claim 1, wherein the chronic brain injury resulted from an acute brain injury.

13. The method of claim 1, wherein an initial dose is followed by one subsequent dose.

14. The method of claim 1, wherein an initial dose is followed by two subsequent doses.

15. The method of claim 1, wherein the etanercept isa dimeric fusion protein consisting of two soluble TNF receptors fused to a Fc portion of an immunoglobulin molecule.

* * * * *